(12) United States Patent
Doi et al.

(10) Patent No.: US 6,872,564 B1
(45) Date of Patent: Mar. 29, 2005

(54) METHOD OF PRODUCING COPOLYMER POLYESTER

(75) Inventors: Yoshiharu Doi, Saitama (JP); Hiromi Matsusaki, Saitama (JP)

(73) Assignee: Japan Science and Technology Corporation, and Riken, Saitama (JP)

( * ) Notice: Subject to any disclaimer, the term of this patent is extended or adjusted under 35 U.S.C. 154(b) by 45 days.

(21) Appl. No.: 09/807,123

(22) PCT Filed: Aug. 9, 2000

(86) PCT No.: PCT/JP00/05331

§ 371 (c)(1), (2), (4) Date: Apr. 5, 2001

(87) PCT Pub. No.: WO01/11014

PCT Pub. Date: Feb. 15, 2001

(30) Foreign Application Priority Data

Aug. 9, 1999 (JP) .......................................... 11/225102

(51) Int. Cl.$^7$ .............................. C12N 1/20; C12P 5/00
(52) U.S. Cl. .............................. 435/252.3; 435/252.33; 435/252.34; 435/6; 435/69.1; 435/166; 435/170; 536/23.1; 536/23.2
(58) Field of Search ................................ 435/166, 170, 435/252.3, 252.34, 253.3, 829, 6; 536/23.1, 23.2

(56) References Cited

U.S. PATENT DOCUMENTS 5,602,321 A 2/1997 John .......................... 800/205

FOREIGN PATENT DOCUMENTS

EP 0 897 005 2/1999 .......... C12N/15/52

OTHER PUBLICATIONS

Matsusaki, H., et al., "Cloning and Molecular Analysis of the Poly(3–hydroxybutyrate) and Poly(3–hydroxybutyrate–co–3–hydroxyalkanoate) Biosynthesis Genes in Pseudomonas sp. Strain 61–3," Journal of Bacteriology (1998) vol. 180, No. 24, pp. 6459–6467.

Peoples, O., et al., "Poly–β–hydroxybutyrate Biosynthesis in Alcaligenes eutrophus H16, " The Journal of Biological Chemistry (1989) vol. 264, No. 26, pp. 15293–15297.

Matsusaki, H., et al., "Biosynthesis of poly(3–hydroxyybutyrate–co–3–hydroxyalkanoates) by recombinant bacteria expressing the PHA synthase gene phaC1 from Pseudomonas sp. 61–3," Applied Microbiology and Biotechnology (2000) vol. 53, No. 4, pp. 401–409.

Abe, et al., "Biosynthesis from gluconate of a random copolyester consisting of 3–hydroxy–butyrate and medium–chain–length 3–hydroxyalkanoates by pseudomonas sp. 61–3", Int. J. Biol. Macromol., vol. 16, No. 3, pp. 115–119, Jun., 1994.

Steinbuchel, et al., "Bacterial and other biological systems for polyester production", Trends in Biotechnology, Elsevier Publications, vol. 16, No. 10, pp. 419–427, Oct. 1, 1998.

Primary Examiner—Richard Hutson
(74) Attorney, Agent, or Firm—Fish & Richardson P.C.

(57) ABSTRACT

A transformant, whose polyhydroxybutanoic acid polymerase gene is disrupted, having a recombinant vector containing a polyester polymerase gene, a β-ketothiolase gene, and a NADPH-acetoacetyl CoA reductase gene.

9 Claims, 9 Drawing Sheets ical material. For example, random copolymer polyester P(3HB-co-3HV) of 3HB and 3-hydroxyvaleric acid (3HV) with a carbon number of 5, also known as Biopol™, is synthesized by cultivation the bacteria *Ralstonia eutropha* (previously known as *Alcaligenes eutrophus*) in medium supplemented with glucose as a carbon source and propionic acid (European Patent Application No. 0052459, 1981). In addition, a random copolymer P(3HB-co-3HH) of 3HB and 3-hydroxyhexanoic acid

SEQUENCE LISTING

<160> NUMBER OF SEQ ID NOS: 11

<210> SEQ ID NO 1
<211> LENGTH: 1680
<212> TYPE: DNA
<213> ORGANISM: Pseudomonas sp. strain 61-3
<220> FEATURE:
<221> NAME/KEY: CDS
<222> LOCATION: (1)..(1677)

<400> SEQUENCE: 1

```
atg agt aac aag aat agc gat gac ttg aat cgt caa gcc tcg gaa aac      48
Met Ser Asn Lys Asn Ser Asp Asp Leu Asn Arg Gln Ala Ser Glu Asn
 1               5                  10                  15 acc ttg ggg ctt aac cct gtc atc ggc ctg cgt gga aaa gat ctg ctg      96
Thr Leu Gly Leu Asn Pro Val Ile Gly Leu Arg Gly Lys Asp Leu Leu
             20                  25                  30 act tct gcc cga atg gtt tta acc caa gcc atc aaa caa ccc att cac     144
Thr Ser Ala Arg Met Val Leu Thr Gln Ala Ile Lys Gln Pro Ile His
         35                  40                  45 agc gtc aag cac gtc gcg cat ttt ggc atc gag ctg aag aac gtg atg     192
Ser Val Lys His Val Ala His Phe Gly Ile Glu Leu Lys Asn Val Met
     50                  55                  60 ttt ggc aaa tcg aag ctg caa ccg gaa agc gat gac cgt cgt ttc aac     240
Phe Gly Lys Ser Lys Leu Gln Pro Glu Ser Asp Asp Arg Arg Phe Asn
 65                  70                  75                  80 gac ccc gcc tgg agt cag aac cca ctc tac aaa cgt tat cta caa acc     288
Asp Pro Ala Trp Ser Gln Asn Pro Leu Tyr Lys Arg Tyr Leu Gln Thr
                 85                  90                  95 tac ctg gcg tgg cgc aag gaa ctc cac gac tgg atc ggc aac agc aaa     336
Tyr Leu Ala Trp Arg Lys Glu Leu His Asp Trp Ile Gly Asn Ser Lys
            100                 105                 110 ctg tcc gaa cag gac atc aat cgc gct cac ttc gtg atc acc ctg atg     384
Leu Ser Glu Gln Asp Ile Asn Arg Ala His Phe Val Ile Thr Leu Met
        115                 120                 125 acc gaa gcc atg gcc ccg acc aac agt gcg gcc aat ccg gcg gcg gtc     432
Thr Glu Ala Met Ala Pro Thr Asn Ser Ala Ala Asn Pro Ala Ala Val
    130                 135                 140 aaa cgc ttc ttc gaa acc ggc ggt aaa agc ctg ctc gac ggc ctc aca     480
Lys Arg Phe Phe Glu Thr Gly Gly Lys Ser Leu Leu Asp Gly Leu Thr
145                 150                 155                 160 cat ctg gcc aag gac ctg gta aac aac ggc ggc atg ccg agc cag gtg     528
His Leu Ala Lys Asp Leu Val Asn Asn Gly Gly Met Pro Ser Gln Val
```

-continued

```
                    165                 170                 175
gac atg ggc gct ttc gaa gtc ggc aag agt ctg ggg acg act gaa ggt      576
Asp Met Gly Ala Phe Glu Val Gly Lys Ser Leu Gly Thr Thr Glu Gly
            180                 185                 190 gca gtg gtt ttc cgc aac gac gtc ctc gaa ttg atc cag tac cgg ccg      624
Ala Val Val Phe Arg Asn Asp Val Leu Glu Leu Ile Gln Tyr Arg Pro
                195                 200                 205 acc acc gaa cag gtg cat gag cga ccg ctg ctg gtg gtc cca ccg cag      672
Thr Thr Glu Gln Val His Glu Arg Pro Leu Leu Val Pro Pro Gln
        210                 215                 220 atc aac aag ttt tat gtg ttt gac ctg agc ccg gat aaa agc ctg gcg      720
Ile Asn Lys Phe Tyr Val Phe Asp Leu Ser Pro Asp Lys Ser Leu Ala
225                 230                 235                 240 cgc ttc tgc ctg agc aac aac cag caa acc ttt atc gtc agc tgg cgc      768
Arg Phe Cys Leu Ser Asn Asn Gln Gln Thr Phe Ile Val Ser Trp Arg
                245                 250                 255 aac ccg acc aag gcc cag cgt gag tgg ggt ctg tcg act tac atc gat      816
Asn Pro Thr Lys Ala Gln Arg Glu Trp Gly Leu Ser Thr Tyr Ile Asp
            260                 265                 270 gcg ctc aaa gaa gcc gtc gac gta gtt tcc gcc atc acc ggc agc aaa      864
Ala Leu Lys Glu Ala Val Asp Val Val Ser Ala Ile Thr Gly Ser Lys
        275                 280                 285 gac atc aac atg ctc ggc gcc tgc tcc ggt ggc att acc tgc acc gcg      912
Asp Ile Asn Met Leu Gly Ala Cys Ser Gly Gly Ile Thr Cys Thr Ala
    290                 295                 300 ctg ctg ggt cac tac gcc gct ctc ggc gag aag aag gtc aat gcc ctg      960
Leu Leu Gly His Tyr Ala Ala Leu Gly Glu Lys Lys Val Asn Ala Leu
305                 310                 315                 320 acc ctt ttg gtc agc gtg ctc gac acc acc ctc gac tcc cag gtt gca     1008
Thr Leu Leu Val Ser Val Leu Asp Thr Thr Leu Asp Ser Gln Val Ala
                325                 330                 335 ctg ttc gtc gat gag aaa acc ctg gaa gct gcc aag cgt cac tcg tat     1056
Leu Phe Val Asp Glu Lys Thr Leu Glu Ala Ala Lys Arg His Ser Tyr
            340                 345                 350 cag gcc ggc gtg ctg gaa ggc cgc gac atg gcc aaa gtc ttc gcc tgg     1104
Gln Ala Gly Val Leu Glu Gly Arg Asp Met Ala Lys Val Phe Ala Trp
        355                 360                 365 atg cgc cct aac gac ctg atc tgg aac tac tgg gtc aac aac tac ctg     1152
Met Arg Pro Asn Asp Leu Ile Trp Asn Tyr Trp Val Asn Asn Tyr Leu
    370                 375                 380 ctg ggt aac gag cca ccg gtc ttc gac att ctt ttc tgg aac aac gac     1200
Leu Gly Asn Glu Pro Pro Val Phe Asp Ile Leu Phe Trp Asn Asn Asp
385                 390                 395                 400 acc acc cgg ttg cct gct gcg ttc cac ggc gat ctg atc gaa atg ttc     1248
Thr Thr Arg Leu Pro Ala Ala Phe His Gly Asp Leu Ile Glu Met Phe
                405                 410                 415 aaa aat aac cca ctg gtg cgc gcc aat gca ctc gaa gtg agc ggc acg     1296
Lys Asn Asn Pro Leu Val Arg Ala Asn Ala Leu Glu Val Ser Gly Thr
            420                 425                 430 ccg atc gac ctc aaa cag gtc act gcc gac atc tac tcc ctg gcc ggc     1344
Pro Ile Asp Leu Lys Gln Val Thr Ala Asp Ile Tyr Ser Leu Ala Gly
        435                 440                 445 acc aac gat cac atc acg ccc tgg aag tct tgc tac aag tcg gcg caa     1392
Thr Asn Asp His Ile Thr Pro Trp Lys Ser Cys Tyr Lys Ser Ala Gln
    450                 455                 460 ctg ttc ggt ggc aag gtc gaa ttc gtg ctg tcc agc agt ggg cat atc     1440
Leu Phe Gly Gly Lys Val Glu Phe Val Leu Ser Ser Ser Gly His Ile
465                 470                 475                 480 cag agc att ctg aac ccg ccg ggc aat ccg aaa tca cgt tac atg acc     1488
```

```
                Gln Ser Ile Leu Asn Pro Pro Gly Asn Pro Lys Ser Arg Tyr Met Thr
                                485                 490                 495 agc acc gac atg cca gcc acc gcc aac gag tgg caa gaa aac tca acc              1536
Ser Thr Asp Met Pro Ala Thr Ala Asn Glu Trp Gln Glu Asn Ser Thr
                500                 505                 510 aag cac acc gac tcc tgg tgg ctg cac tgg cag gcc tgg cag gcc gag              1584
Lys His Thr Asp Ser Trp Trp Leu His Trp Gln Ala Trp Gln Ala Glu
            515                 520                 525 cgc tcg ggc aaa ctg aaa aag tcc ccg acc agc ctg ggc aac aag gcc              1632
Arg Ser Gly Lys Leu Lys Lys Ser Pro Thr Ser Leu Gly Asn Lys Ala
        530                 535                 540 tat ccg tca gga gaa gcc gcg ccg ggc acg tat gtg cat gaa cgt taa              1680
Tyr Pro Ser Gly Glu Ala Ala Pro Gly Thr Tyr Val His Glu Arg
545                 550                 555

<210> SEQ ID NO 2
<211> LENGTH: 559
<212> TYPE: PRT
<213> ORGANISM: Pseudomonas sp. strain 61-3

<400> SEQUENCE: 2

Met Ser Asn Lys Asn Ser Asp Asp Leu Asn Arg Gln Ala Ser Glu Asn
  1               5                  10                  15

Thr Leu Gly Leu Asn Pro Val Ile Gly Leu Arg Gly Lys Asp Leu Leu
                 20                  25                  30

Thr Ser Ala Arg Met Val Leu Thr Gln Ala Ile Lys Gln Pro Ile His
             35                  40                  45

Ser Val Lys His Val Ala His Phe Gly Ile Glu Leu Lys Asn Val Met
         50                  55                  60

Phe Gly Lys Ser Lys Leu Gln Pro Glu Ser Asp Asp Arg Arg Phe Asn
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Val Ser Ala Ile Thr Gly Ser Lys
```

-continued

```
                       275                 280                 285
Asp Ile Asn Met Leu Gly Ala Cys Ser Gly Ile Thr Cys Thr Ala
    290                 295                 300
Leu Leu Gly His Tyr Ala Ala Leu Gly Glu Lys Lys Val Asn Ala Leu
305                 310                 315                 320
Thr Leu Leu Val Ser Val Leu Asp Thr Thr Leu Asp Ser Gln Val Ala
                325                 330                 335
Leu Phe Val Asp Glu Lys Thr Leu Glu Ala Ala Lys Arg His Ser Tyr
            340                 345                 350
Gln Ala Gly Val Leu Glu Gly Arg Asp Met Ala Lys Val Phe Ala Trp
        355                 360                 365
Met Arg Pro Asn Asp Leu Ile Trp Asn Tyr Trp Val Asn Asn Tyr Leu
    370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Met Phe
                405                 410                 415
Lys Asn Asn Pro Leu Val Arg Ala Asn Ala Leu Glu Val Ser Gly Thr
            420                 425                 430
Pro Ile Asp Leu Lys Gln Val Thr Ala Asp Ile Tyr Ser Leu Ala Gly
        435                 440                 445
Thr Asn Asp His Ile Thr Pro Trp Lys Ser Cys Tyr Lys Ser Ala Gln
    450                 455                 460
Leu Phe Gly Gly Lys Val Glu Phe Val Leu Ser Ser Ser Gly His Ile
465                 470                 475                 480
Gln Ser Ile Leu Asn Pro Pro Gly Asn Pro Lys Ser Arg Tyr Met Thr
                485                 490                 495
Ser Thr Asp Met Pro Ala Thr Ala Asn Glu Trp Gln Glu Asn Ser Thr
            500                 505                 510
Lys His Thr Asp Ser Trp Trp Leu His Trp Gln Ala Trp Gln Ala Glu
        515                 520                 525
Arg Ser Gly Lys Leu Lys Lys Ser Pro Thr Ser Leu Gly Asn Lys Ala
    530                 535                 540
Tyr Pro Ser Gly Glu Ala Ala Pro Gly Thr Tyr Val His Glu Arg
545                 550                 555
```

<210> SEQ ID NO 3
<211> LENGTH: 1683
<212> TYPE: DNA
<213> ORGANISM: Pseudomonas sp. strain 61-3
<220> FEATURE:
<221> NAME/KEY: CDS
<222> LOCATION: (1)..(1680)

<400> SEQUENCE: 3

```
atg aga gag aaa cca acg ccg ggc ttg ctg ccc aca ccc gcg acg ttc      48
Met Arg Glu Lys Pro Thr Pro Gly Leu Leu Pro Thr Pro Ala Thr Phe
  1               5                  10                  15 atc aac gct cag agt gcg att acc ggt ctg cgc ggc cgg gat ctg ttc      96
Ile Asn Ala Gln Ser Ala Ile Thr Gly Leu Arg Gly Arg Asp Leu Phe
                 20                  25                  30 tcg acc ctg cgc agc gtg gcc gcc cac ggc ctg cgt cac ccg gtg cgc     144
Ser Thr Leu Arg Ser Val Ala Ala His Gly Leu Arg His Pro Val Arg
             35                  40                  45 agc gcc cgt cat gtt ctg gca ctg ggc ggc cag ttg ggc cgc gtg ctg     192
Ser Ala Arg His Val Leu Ala Leu Gly Gly Gln Leu Gly Arg Val Leu
         50                  55                  60
```

-continued

| | |
|---|---|
| ctg ggc gaa acg ctg cac acg ccg aac ccg aaa gac aat cgc ttt gcg<br>Leu Gly Glu Thr Leu His Thr Pro Asn Pro Lys Asp Asn Arg Phe Ala<br>65                       70                     75                     80 | 240 |
| gac ccg acc tgg aga ctg aat ccg ttt tac cgg cgc agc ctg cag gcc<br>Asp Pro Thr Trp Arg Leu Asn Pro Phe Tyr Arg Arg Ser Leu Gln Ala<br>                    85                     90                     95 | 288 |
| tat ctg agc tgg cag aaa cag gtc aaa agc tgg atc gat gaa agc ggc<br>Tyr Leu Ser Trp Gln Lys Gln Val Lys Ser Trp Ile Asp Glu Ser Gly<br>             100                     105                     110 | 336 |
| atg agt gac gat gac cgc gcc cgc gcg cat ttc gtc ttc gca ctg ctc<br>Met Ser Asp Asp Asp Arg Ala Arg Ala His Phe Val Phe Ala Leu Leu<br>115                     120                     125 | 384 |
| aat gac gcc gtg tcc ccc tcc aat acc ctg ctc aac ccg cta gcg atc<br>Asn Asp Ala Val Ser Pro Ser Asn Thr Leu Leu Asn Pro Leu Ala Ile<br>130                     135                     140 | 432 |
| aag gag ctg ttc aac tcc ggt ggc aac agc ctg gtc cgc ggt ctc agc<br>Lys Glu Leu Phe Asn Ser Gly Gly Asn Ser Leu Val Arg Gly Leu Ser<br>145                     150                     155                     160 | 480 |
| cat tta ttc gac gac ctg atg cac aac aac ggg ctg ccc agt cag gtc<br>His Leu Phe Asp Asp Leu Met His Asn Asn Gly Leu Pro Ser Gln Val<br>                    165                     170                     175 | 528 |
| acc aaa cac gcc ttc gag att ggc aag acc gtg gca acc acc gcc ggg<br>Thr Lys His Ala Phe Glu Ile Gly Lys Thr Val Ala Thr Thr Ala Gly<br>                    180                     185                     190 | 576 |
| tcc gtg gtg ttt cgc aac gag ctg ctc gag ctg atg cag tac aag ccg<br>Ser Val Val Phe Arg Asn Glu Leu Leu Glu Leu Met Gln Tyr Lys Pro<br>              195                     200                     205 | 624 |
| atg agc gaa aaa cag tac gcc aag ccg ttg ctg atc gtc ccg ccg cag<br>Met Ser Glu Lys Gln Tyr Ala Lys Pro Leu Leu Ile Val Pro Pro Gln<br>210                     215                     220 | 672 |
| att aac aag tac tac att ttc gac ctc agc ccg ggt aac agc ttc gtc<br>Ile Asn Lys Tyr Tyr Ile Phe Asp Leu Ser Pro Gly Asn Ser Phe Val<br>225                     230                     235                     240 | 720 |
| cag tac gca ttg aag aat ggt ctg cag gtg ttc gtg gtc agc tgg cgt<br>Gln Tyr Ala Leu Lys Asn Gly Leu Gln Val Phe Val Val Ser Trp Arg<br>                    245                     250                     255 | 768 |
| aac ccg gat gtt cgc cac cgc gaa tgg ggc ctg tcc agt tac gtt gag<br>Asn Pro Asp Val Arg His Arg Glu Trp Gly Leu Ser Ser Tyr Val Glu<br>                    260                     265                     270 | 816 |
| gca ctg gaa gaa gca ctg aat gtt tgc cgc gct atc acc ggc gcg cgc<br>Ala Leu Glu Glu Ala Leu Asn Val Cys Arg Ala Ile Thr Gly Ala Arg<br>             275                     280                     285 | 864 |
| gac gtc aat ctg atg ggc gcc tgt gct ggc ggc ctg acc atc gcg gct<br>Asp Val Asn Leu Met Gly Ala Cys Ala Gly Gly Leu Thr Ile Ala Ala<br>290                     295                     300 | 912 |
| ctg caa ggt cat ctg caa gcc aag cgg caa ctg cgg cgg gtc tcc agc<br>Leu Gln Gly His Leu Gln Ala Lys Arg Gln Leu Arg Arg Val Ser Ser<br>305                     310                     315                     320 | 960 |
| gcc agc tac ctg gtc agc ctg ctg gat agc cag ata gac agc ccg gcg<br>Ala Ser Tyr Leu Val Ser Leu Leu Asp Ser Gln Ile Asp Ser Pro Ala<br>                    325                     330                     335 | 1008 |
| acg ttg ttc gcc gat gag cag acg ctg gaa gcc gcc aag cgc cat tcc<br>Thr Leu Phe Ala Asp Glu Gln Thr Leu Glu Ala Ala Lys Arg His Ser<br>                    340                     345                     350 | 1056 |
| tat caa cga ggt gtg ctc gag ggg cgc gac atg gcg aaa atc ttc gcc<br>Tyr Gln Arg Gly Val Leu Glu Gly Arg Asp Met Ala Lys Ile Phe Ala<br>             355                     360                     365 | 1104 |
| tgg atg cgc ccc aat gac ctg atc tgg aac tac tgg gtc aac aac tac<br>Trp Met Arg Pro Asn Asp Leu Ile Trp Asn Tyr Trp Val Asn Asn Tyr | 1152 |

```
                    370                 375                 380
ctg ctg ggc aaa gaa ccg ccg gcc ttc gac att ctg tat tgg aac agt    1200
Leu Leu Gly Lys Glu Pro Pro Ala Phe Asp Ile Leu Tyr Trp Asn Ser
385                 390                 395                 400 gac aac acg cgc ctg cca gcg gca ttc cat ggc gac ctg ctg gac ttc    1248
Asp Asn Thr Arg Leu Pro Ala Ala Phe His Gly Asp Leu Leu Asp Phe
            405                 410                 415 ttc aag cac aat ccg ctg act cac ccc ggc ggg ctg gag gtc tgt ggc    1296
Phe Lys His Asn Pro Leu Thr His Pro Gly Gly Leu Glu Val Cys Gly
        420                 425                 430 acg cct atc gat ttg cag aag gtc aac gta gac agc ttc agc gtg gcc    1344
Thr Pro Ile Asp Leu Gln Lys Val Asn Val Asp Ser Phe Ser Val Ala
    435                 440                 445 ggc atc aac gac cac atc act ccg tgg gac gcg gtg tac cgc tcg acc    1392
Gly Ile Asn Asp His Ile Thr Pro Trp Asp Ala Val Tyr Arg Ser Thr
450                 455                 460 ctg ctg ctg ggt ggc gac cgg cgc ttc gta ctg tcc aac agc ggg cat    1440
Leu Leu Leu Gly Gly Asp Arg Arg Phe Val Leu Ser Asn Ser Gly His
465                 470                 475                 480 atc cag agc atc ctc aac ccg ccg agc aac ccc aag tcc aac tac atc    1488
Ile Gln Ser Ile Leu Asn Pro Pro Ser Asn Pro Lys Ser Asn Tyr Ile
            485                 490                 495 gag aac ccc aag ctc agt ggc gat cca cgc gcc tgg tat tac gac ggc    1536
Glu Asn Pro Lys Leu Ser Gly Asp Pro Arg Ala Trp Tyr Tyr Asp Gly
        500                 505                 510 acc cat gtc gaa ggt agc tgg tgg cca cgt tgg ctg agc tgg att cag    1584
Thr His Val Glu Gly Ser Trp Trp Pro Arg Trp Leu Ser Trp Ile Gln
    515                 520                 525 gag cgc tcc ggt acc caa cgc gaa acc ctg atg gcc ctt ggt aac cag    1632
Glu Arg Ser Gly Thr Gln Arg Glu Thr Leu Met Ala Leu Gly Asn Gln
530                 535                 540 aac tat cca ccg atg gag gcg gcg cca ggt acc tac gtg cgc gtg cgc    1680
Asn Tyr Pro Pro Met Glu Ala Ala Pro Gly Thr Tyr Val Arg Val Arg
545                 550                 555                 560 tga                                                                 1683
```

<210> SEQ ID NO 4
<211> LENGTH: 560
<212> TYPE: PRT
<213> ORGANISM: Pseudomonas sp. strain 61-3

<400> SEQUENCE: 4

```
Met Arg Glu Lys Pro Thr Pro Gly Leu Leu Pro Thr Pro Ala Thr Phe
  1               5                  10                  15

Ile Asn Ala Gln Ser Ala Ile Thr Gly Leu Arg Gly Arg Asp Leu Phe
             20                  25                  30

Ser Thr Leu Arg Ser Val Ala Ala His Gly Leu Arg His Pro Val Arg
         35                  40                  45

Ser Ala Arg His Val Leu Ala Leu Gly Gly Gln Leu Gly Arg Val Leu
     50                  55                  60

Leu Gly Glu Thr Leu His Thr Pro Asn Pro Lys Asp Asn Arg Phe Ala
 65                  70                  75                  80

Asp Pro Thr Trp Arg Leu Asn Pro Phe Tyr Arg Arg Ser Leu Gln Ala
                 85                  90                  95

Tyr Leu Ser Trp Gln Lys Gln Val Lys Ser Trp Ile Asp Glu Ser Gly
            100                 105                 110

Met Ser Asp Asp Asp Arg Ala Arg Ala His Phe Val Phe Ala Leu Leu
        115                 120                 125
```

```
Asn Asp Ala Val Ser Pro Ser Asn Thr Leu Leu Asn Pro Leu Ala Ile
130                 135                 140

Lys Glu Leu Phe Asn Ser Gly Gly Asn Ser Leu Val Arg Gly Leu Ser
145                 150                 155                 160

His Leu Phe Asp Asp Leu Met His Asn Asn Gly Leu Pro Ser Gln Val
                165                 170                 175

Thr Lys His Ala Phe Glu Ile Gly Lys Thr Val Ala Thr Thr Ala Gly
            180                 185                 190

Ser Val Val Phe Arg Asn Glu Leu Leu Glu Leu Met Gln Tyr Lys Pro
        195                 200                 205

Met Ser Glu Lys Gln Tyr Ala Lys Pro Leu Leu Ile Val Pro Pro Gln
210                 215                 220

Ile Asn Lys Tyr Tyr Ile Phe Asp Leu Ser Pro Gly Asn Ser Phe Val
225                 230                 235                 240

Gln Tyr Ala Leu Lys Asn Gly Leu Gln Val Phe Val Ser Trp Arg
                245                 250                 255

Asn Pro Asp Val Arg His Arg Glu Trp Gly Leu Ser Ser Tyr Val Glu
                260                 265                 270

Ala Leu Glu Glu Ala Leu Asn Val Cys Arg Ala Ile Thr Gly Ala Arg
        275                 280                 285

Asp Val Asn Leu Met Gly Ala Cys Ala Gly Gly Leu Thr Ile Ala Ala
        290                 295                 300

Leu Gln Gly His Leu Gln Ala Lys Arg Gln Leu Arg Arg Val Ser Ser
305                 310                 315                 320

Ala Ser Tyr Leu Val Ser Leu Leu Asp Ser Gln Ile Asp Ser Pro Ala
            325                 330                 335

Thr Leu Phe Ala Asp Glu Gln Thr Leu Glu Ala Ala Lys Arg His Ser
            340                 345                 350

Tyr Gln Arg Gly Val Leu Glu Gly Arg Asp Met Ala Lys Ile Phe Ala
        355                 360                 365

Trp Met Arg Pro Asn Asp Leu Ile Trp Asn Tyr Trp Val Asn Asn Tyr
370                 375                 380

Leu Leu Gly Lys Glu Pro Pro Ala Phe Asp Ile Leu Tyr Trp Asn Ser
385                 390                 395                 400

Asp Asn Thr Arg Leu Pro Ala Ala Phe His Gly Asp Leu Leu Asp Phe
                405                 410                 415

Phe Lys His Asn Pro Leu Thr His Pro Gly Gly Leu Glu Val Cys Gly
            420                 425                 430

Thr Pro Ile Asp Leu Gln Lys Val Asn Val Asp Ser Phe Ser Val Ala
            435                 440                 445

Gly Ile Asn Asp His Ile Thr Pro Trp Asp Ala Val Tyr Arg Ser Thr
450                 455                 460

Leu Leu Leu Gly Gly Asp Arg Arg Phe Val Leu Ser Asn Ser Gly His
465                 470                 475                 480

Ile Gln Ser Ile Leu Asn Pro Pro Ser Asn Pro Lys Ser Asn Tyr Ile
            485                 490                 495

Glu Asn Pro Lys Leu Ser Gly Asp Pro Arg Ala Trp Tyr Tyr Asp Gly
            500                 505                 510

Thr His Val Glu Gly Ser Trp Trp Pro Arg Trp Leu Ser Trp Ile Gln
        515                 520                 525

Glu Arg Ser Gly Thr Gln Arg Glu Thr Leu Met Ala Leu Gly Asn Gln
530                 535                 540
```

```
Asn Tyr Pro Pro Met Glu Ala Ala Pro Gly Thr Tyr Val Arg Val Arg
545                 550                 555                 560

<210> SEQ ID NO 5
<211> LENGTH: 1179
<212> TYPE: DNA
<213> ORGANISM: Ralstonia eutropha
<220> FEATURE:
<221> NAME/KEY: CDS
<222> LOCATION: (1)..(1179)

<400> SEQUENCE: 5 atg act gac gtt gtc atc gta tcc gcc gcc cgc acc gcg gtc ggc aag     48
Met Thr Asp Val Val Ile Val Ser Ala Ala Arg Thr Ala Val Gly Lys
 1               5                  10                  15 ttt ggc ggc tcg ctg gcc aag atc ccg gca ccg gaa ctg ggt gcc gtg     96
Phe Gly Gly Ser Leu Ala Lys Ile Pro Ala Pro Glu Leu Gly Ala Val
             20                  25                  30 gtc atc aag gcc gcg ctg gag cgc gcc ggc gtc aag ccg gag cag gtg    144
Val Ile Lys Ala Ala Leu Glu Arg Ala Gly Val Lys Pro Glu Gln Val
         35                  40                  45 agc gaa gtc atc atg ggc cag gtg ctg acc gcc ggt tcg ggc cag aac    192
Ser Glu Val Ile Met Gly Gln Val Leu Thr Ala Gly Ser Gly Gln Asn
     50                  55                  60 ccc gca cgc cag gcc gcg atc aag gcc ggc ctg ccg gcg atg gtg ccg    240
Pro Ala Arg Gln Ala Ala Ile Lys Ala Gly Leu Pro Ala Met Val Pro
 65                  70                  75                  80 gcc atg acc atc aac aag gtg tgc ggc tcg ggc ctg aag gcc gtg atg    288
Ala Met Thr Ile Asn Lys Val Cys Gly Ser Gly Leu Lys Ala Val Met
                 85                  90                  95 ctg gcc gcc aac gcg atc atg gcg ggc gac gcc gag atc gtg gtg gcc    336
Leu Ala Ala Asn Ala Ile Met Ala Gly Asp Ala Glu Ile Val Val Ala
            100                 105                 110 ggc ggc cag gaa aac atg agc gcc gcc ccg cac gtg ctg ccg ggc tcg    384
Gly Gly Gln Glu Asn Met Ser Ala Ala Pro His Val Leu Pro Gly Ser
        115                 120                 125 cgc gat ggt ttc cgc atg ggc gat gcc aag ctg gtc gac acc atg atc    432
Arg Asp Gly Phe Arg Met Gly Asp Ala Lys Leu Val Asp Thr Met Ile
    130                 135                 140 gtc gac ggc ctg tgg gac gtg tac aac cag tac cac atg ggc atc acc    480
Val Asp Gly Leu Trp Asp Val Tyr Asn Gln Tyr His Met Gly Ile Thr
145                 150                 155                 160 gcc gag aac gtg gcc aag gaa tac ggc atc aca cgc gag gcg cag gat    528
Ala Glu Asn Val Ala Lys Glu Tyr Gly Ile Thr Arg Glu Ala Gln Asp
                165                 170                 175 gag ttc gcc gtc ggc tcg cag aac aag gcc gaa gcc gcg cag aag gcc    576
Glu Phe Ala Val Gly Ser Gln Asn Lys Ala Glu Ala Ala Gln Lys Ala
            180                 185                 190 ggc aag ttt gac gaa gag atc gtc ccg gtg ctg atc ccg cag cgc aag    624
Gly Lys Phe Asp Glu Glu Ile Val Pro Val Leu Ile Pro Gln Arg Lys
        195                 200                 205 ggc gac ccg gtg gcc ttc aag acc gac gag ttc gtg cgc cag ggc gcc    672
Gly Asp Pro Val Ala Phe Lys Thr Asp Glu Phe Val Arg Gln Gly Ala
    210                 215                 220 acg ctg gac agc atg tcc ggc ctc aag ccc gcc ttc gac aag gcc ggc    720
Thr Leu Asp Ser Met Ser Gly Leu Lys Pro Ala Phe Asp Lys Ala Gly
225                 230                 235                 240 acg gtg acc gcg gcc aac gcc tcg ggc ctg aac gac ggc gcc gcc gcg    768
Thr Val Thr Ala Ala Asn Ala Ser Gly Leu Asn Asp Gly Ala Ala Ala
                245                 250                 255 gtg gtg gtg atg tcg gcg gcc aag gcc aag gaa ctg ggc ctg acc ccg    816
```

-continued

```
Val Val Val Met Ser Ala Ala Lys Ala Lys Glu Leu Gly Leu Thr Pro
            260                 265                 270
ctg gcc acg atc aag agc tat gcc aac gcc ggt gtc gat ccc aag gtg    864
Leu Ala Thr Ile Lys Ser Tyr Ala Asn Ala Gly Val Asp Pro Lys Val
        275                 280                 285
atg ggc atg ggc ccg gtg ccg gcc tcc aag cgc gcc ctg tcg cgc gcc    912
Met Gly Met Gly Pro Val Pro Ala Ser Lys Arg Ala Leu Ser Arg Ala
    290                 295                 300
gag tgg acc ccg caa gac ctg gac ctg atg gag atc aac gag gcc ttt    960
Glu Trp Thr Pro Gln Asp Leu Asp Leu Met Glu Ile Asn Glu Ala Phe
305                 310                 315                 320
gcc gcg cag gcg ctg gcg gtg cac cag cag atg ggc tgg gac acc tcc   1008
Ala Ala Gln Ala Leu Ala Val His Gln Gln Met Gly Trp Asp Thr Ser
                325                 330                 335
aag gtc aat gtg aac ggc ggc gcc atc gcc atc ggc cac ccg atc ggc   1056
Lys Val Asn Val Asn Gly Gly Ala Ile Ala Ile Gly His Pro Ile Gly
            340                 345                 350
gcg tcg ggc tgc cgt atc ctg gtg acg ctg ctg cac gag atg aag cgc   1104
Ala Ser Gly Cys Arg Ile Leu Val Thr Leu Leu His Glu Met Lys Arg
        355                 360                 365
cgt gac gcg aag aag ggc ctg gcc tcg ctg tgc atc ggc ggc ggc atg   1152
Arg Asp Ala Lys Lys Gly Leu Ala Ser Leu Cys Ile Gly Gly Gly Met
370                 375                 380
ggc gtg gcg ctg gca gtc gag cgc aaa                               1179
Gly Val Ala Leu Ala Val Glu Arg Lys
385                 390
```

<210> SEQ ID NO 6
<211> LENGTH: 393
<212> TYPE: PRT
<213> ORGANISM: Ralstonia eutropha

<400> SEQUENCE: 6

```
Met Thr Asp Val Val Ile Val Ser Ala Ala Arg Thr Ala Val Gly Lys
  1               5                  10                  15

Phe Gly Gly Ser Leu Ala Lys Ile Pro Ala Pro Glu Leu Gly Ala Val
             20                  25                  30

Val Ile Lys Ala Ala Leu Glu Arg Ala Gly Val Lys Pro Glu Gln Val
         35                  40                  45

Ser Glu Val Ile Met Gly Gln Val Leu Thr Ala Gly Ser Gly Gln Asn
     50                  55                  60

Pro Ala Arg Gln Ala Ala Ile Lys Ala Gly Leu Pro Ala Met Val Pro
 65                  70                  75                  80

Ala Met Thr Ile Asn Lys Val Cys Gly Ser Gly Leu Lys Ala Val Met
                 85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190
```

```
Gly Lys Phe Asp Glu Ile Val Pro Val Leu Ile Pro Gln Arg Lys
        195                 200                 205

Gly Asp Pro Val Ala Phe Lys Thr Asp Glu Phe Val Arg Gln Gly Ala
210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390

<210> SEQ ID NO 7
<211> LENGTH: 738
<212> TYPE: DNA
<213> ORGANISM: Ralstonia eutropha
<220> FEATURE:
<221> NAME/KEY: CDS
<222> LOCATION: (1)..(738)

<400> SEQUENCE: 7 atg act cag cgc att gcg tat gtg acc ggc ggc atg ggt ggt atc gga    48
Met Thr Gln Arg Ile Ala Tyr Val Thr Gly Gly Met Gly Gly Ile Gly
  1               5                  10                  15 acc gcc att tgc cag cgg ctg gcc aag gat ggc ttt cgt gtg gtg gcc    96
Thr Ala Ile Cys Gln Arg Leu Ala Lys Asp Gly Phe Arg Val Val Ala
                 20                  25                  30 ggt tgc ggc ccc aac tcg ccg cgc cgc gaa aag tgg ctg gag cag cag   144
Gly Cys Gly Pro Asn Ser Pro Arg Arg Glu Lys Trp Leu Glu Gln Gln
             35                  40                  45 aag gcc ctg ggc ttc gat ttc att gcc tcg gaa ggc aat gtg gct gac   192
Lys Ala Leu Gly Phe Asp Phe Ile Ala Ser Glu Gly Asn Val Ala Asp
         50                  55                  60 tgg gac tcg acc aag acc gca ttc gac aag gtc aag tcc gag gtc ggc   240
Trp Asp Ser Thr Lys Thr Ala Phe Asp Lys Val Lys Ser Glu Val Gly
 65                  70                  75                  80 gag gtt gat gtg ctg atc aac aac gcc ggt atc acc cgc gac gtg gtg   288
Glu Val Asp Val Leu Ile Asn Asn Ala Gly Ile Thr Arg Asp Val Val
                 85                  90                  95 ttc cgc aag atg acc cgc gcc gac tgg gat gcg gtg atc gac acc aac   336
Phe Arg Lys Met Thr Arg Ala Asp Trp Asp Ala Val Ile Asp Thr Asn
                100                 105                 110 ctg acc tcg ctg ttc aac gtc acc aag cag gtg atc gac ggc atg gcc   384
```

```
Leu Thr Ser Leu Phe Asn Val Thr Lys Gln Val Ile Asp Gly Met Ala
            115                 120                 125 gac cgt ggc tgg ggc cgc atc gtc aac atc tcg tcg gtg aac ggg cag      432
Asp Arg Gly Trp Gly Arg Ile Val Asn Ile Ser Ser Val Asn Gly Gln
        130                 135                 140 aag ggc cag ttc ggc cag acc aac tac tcc acc gcc aag gcc ggc ctg      480
Lys Gly Gln Phe Gly Gln Thr Asn Tyr Ser Thr Ala Lys Ala Gly Leu
145                 150                 155                 160 cat ggc ttc acc atg gca ctg gcg cag gaa gtg gcg acc aag ggc gtg      528
His Gly Phe Thr Met Ala Leu Ala Gln Glu Val Ala Thr Lys Gly Val
                165                 170                 175 acc gtc aac acg gtc tct ccg ggc tat atc gcc acc gac atg gtc aag      576
Thr Val Asn Thr Val Ser Pro Gly Tyr Ile Ala Thr Asp Met Val Lys
            180                 185                 190 gcg atc cgc cag gac gtg ctc gac aag atc gtc gcg acg atc ccg gtc      624
Ala Ile Arg Gln Asp Val Leu Asp Lys Ile Val Ala Thr Ile Pro Val
        195                 200                 205 aag cgc ctg ggc ctg ccg gaa gag atc gcc tcg atc tgc gcc tgg ttg      672
Lys Arg Leu Gly Leu Pro Glu Glu Ile Ala Ser Ile Cys Ala Trp Leu
210                 215                 220 tcg tcg gag gag tcc ggt ttc tcg acc ggc gcc gac ttc tcg ctc aac      720
Ser Ser Glu Glu Ser Gly Phe Ser Thr Gly Ala Asp Phe Ser Leu Asn
225                 230                 235                 240 ggc ggc ctg cat atg ggc                                              738
Gly Gly Leu His Met Gly
                245

<210> SEQ ID NO 8
<211> LENGTH: 246
<212> TYPE: PRT
<213> ORGANISM: Ralstonia eutropha

<400> SEQUENCE: 8

Met Thr Gln Arg Ile Ala Tyr Val Thr Gly Gly Met Gly Gly Ile Gly
  1               5                  10                  15

Thr Ala Ile Cys Gln Arg Leu Ala Lys Asp Gly Phe Arg Val Val Ala
                20                  25                  30

Gly Cys Gly Pro Asn Ser Pro Arg Arg Glu Lys Trp Leu Glu Gln Gln
            35                  40                  45

Lys Ala Leu Gly Phe Asp Phe Ile Ala Ser Glu Gly Asn Val Ala Asp
        50                  55                  60

Trp Asp Ser Thr Lys Thr Ala Phe Asp Lys Val Lys Ser Glu Val Gly
 65                  70                  75                  80

Glu Val Asp Val Leu Ile Asn Asn Ala Gly Ile Thr Arg Asp Val Val
                    85                  90                  95

Phe Arg Lys Met Thr Arg Ala Asp Trp Asp Ala Val Ile Asp Thr Asn
                100                 105                 110

Leu Thr Ser Leu Phe Asn Val Thr Lys Gln Val Ile Asp Gly Met Ala
            115                 120                 125

Asp Arg Gly Trp Gly Arg Ile Val Asn Ile Ser Ser Val Asn Gly Gln
        130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190
```

```
Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 9
<211> LENGTH: 542
<212> TYPE: DNA
<213> ORGANISM: Pseudomonas sp. strain 61-3

<400> SEQUENCE: 9
gaattcttgc gcgtgcactc tccttccgcc gaagtccagg gccacggcaa acctatcctg     60
caatttggca agatcggcgt aggcctgaac aaggtagaac cggccggtca gtacgcactg    120
aaattgacct tcgacgacgg ccatgacagc ggcctgttca cctgggatta tctgtaccaa    180
ctggcacaac gtcaggaagc actttgggca gattatcttg cagaactcaa agcggctgga    240
aagtcccgcg acccaagcga atccatcgtc aagctgatgc tctaattcag gcctcttgct    300
ctttagaggg cattttctaa tttcatctgt ttgaatgctc cgctgtgcgg caagcgattg    360
gcctgcttgc gaaaaaaatt aaactcgggt aaccaatgga gctggcaagt tccctgcagt    420
gctctctgaa ctagaaagca acgttgtgca attaacggtc acccgagcag tagtacctgg    480
cggttgctgt gtgactacac agctggtccc ggtactcgtc tcaggacaat ggagcgtcgt    540
ag                                                                   542

<210> SEQ ID NO 10
<211> LENGTH: 841
<212> TYPE: DNA
<213> ORGANISM: Ralstonia eutropha

<400> SEQUENCE: 10
cccgggcaag taccttgccg acatctatgc gctggcgcgc acgcgcctgg cgcgcgccgg     60
ctgtaccgag gtctacggcg gcgacgcctg caccgtggcc gacgccggtc gcttctactc    120
ctatcggcgc gatggcgtga ccggccgcat ggccagcctg gtctggctgg cggactgagc    180
ccgccgctgc ctcactcgtc cttgcccctg gccgcctgcg cgcgctcggc ttcagccttg    240
cgtcggcggc ggccgggcgt gcccatgatg tagagcacca cgccaccggc gccatgccat    300
acatcaggaa ggtggcaacg cctgccacca cgttgtgctc ggtgatcgcc atcatcagcg    360
ccacgtagag ccagccaatg ccacgatgt acatcaaaaa ttcatccttc cgcctatgc     420 tctgggccct cggcagatgc gagcgctgca taccgtccgg taggtcggga agcgtgcagt    480
gccgaggcgg attcccgcat tgacagcgcg tgcgttgcaa gcaacaatg gactcaaatg     540 tctcggaatc gctgacgatt cccaggtttc tccggcaagc atagcgcatg cgtctccat     600 gcgagaatgt cgcgcttgcc ggataaaagg ggagccgcta tcggaatgga cgcaagccac    660
ggccgcagca ggtgcggtcg agggcttcca gccagttcca gggcagatgt gccggcagac    720
cctcccgctt tggggaggc gcaagccggg tccattcgga tagcatctcc ccatgcaaag     780
tgccggccag ggcaatgccc ggagccggtt cgaatagtga cggcagagag acaatcaaat    840
c                                                                    841
```

<210> SEQ ID NO 11
<211> LENGTH: 292
<212> TYPE: DNA
<213> ORGANISM: Ralstonia eutropha

<400> SEQUENCE: 11

```
cctgccggcc tggttcaacc agtcggcagc cggcgctggc gcccgcgtat tgcggtgcag      60
ccagcgcggc gcacaaggcg gcgggcgttt cgtttcgccg cccgtttcgc gggccgtcaa     120
ggcccgcgaa tcgtttctgc ccgcgcggca ttcctcgctt tttgcgccaa ttcaccgggt     180
tttccttaag ccccgtcgct tttcttagtg ccttgttggg catagaatca gggcagcggc     240
gcagccagca ccatgttcgt gcagcgcggc cctcgcgggg gcgaggctgc ag             292
```

METHOD OF PRODUCING COPOLYMER POLYESTER

DEPOSIT OF BIOLOGICAL MATERIAL

Under the terms of the Budapest Treaty on the International Recognition of the Deposit of Microorganisms for the Purpose of Patent Procedure, deposit of *Pseudomonas* sp. strain 61-3 was made with the Japan Collection of Microorganisms (JCM) on Jan. 10, 1997. The JCM is a depository at 2-1 Hirosawa, Wako, Saitama 351-0198, JAPAN, where the deposit was given Accession Number 10015 (FERM P-13108).

Applicants represent that the JCM is a depository affording permanence of the deposit and ready accessibility thereto by the public if a patent is granted. All restrictions on the availability to the public of the material so deposited have been irrevocably removed. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants acknowledge their duty to replace the deposit should the depository be unable to furnish a sample when requested due to the condition of the deposit.

FIELD OF THE INVENTION

The present invention relates to a transformant that is obtained by transforming a host, whose polyhydroxybutanoic acid polymerase gene is disrupted, with a recombinant vector containing a polyester polymerase gene, a β-ketothiolase gene, and a NADPH-acetoacetyl CoA reductase gene, and a method of producing copolymer polyester using the transformant.

BACKGROUND OF THE PRESENT INVENTION

BACKGROUND ART

Many microorganisms are known to bio-synthesize poly-3-hydroxybutanoic acid (P(3HB)) and accumulate the fine granular products in its cells as energy storage materials. P(3HB) extracted from microorganisms is a thermoplastic polymer having a melting temperature around 180° C. Currently, P(3HB) is receiving attention as an eco-friendly plastic for environmental conservation because of its good biodegradation ability and biological compatibility. Moreover, P(3HB) can be synthesized from regenerative carbon sources including sugar and vegetable oil using various microorganisms. On the other hand, P(3HB) has a poor impact resistance since it is a high crystallinity polymer. This physical property has hindered the commercialization of P(3HB). However, the impact resistance of P(3HB) can be improved by producing a copolymer of long chain 3-hydroxyalkanoic acid (3HA) units and 3HB unit, so as to produce a flexible material. For example, random copolymer polyester P(3HB-co-3HV) of 3HB and 3-hydroxyvaleric acid (3HV) with a carbon number of 5, also known as Biopol™, is synthesized by cultivation the bacteria *Ralstonia eutropha* (previously known as *Alcaligenes eutrophus*) in medium supplemented with glucose as a carbon source and propionic acid (European Patent Application No. 0052459, 1981). In addition, a random copolymer P(3HB-co-3HH) of 3HB and 3-hydroxyhexanoic acid (3HH) is synthesized by *Aeromonas caviae*. This copolymer and its production method have been studied and developed as described in Japanese Patent Laid Open Publication Nos. 5-93049 and 7-265065. P(3HB-co-3HH) copolymer has been shown to be a flexible polymer material because its crystallinity decreases as 3HH unit composition increases. Furthermore, P(3HB-co-3HH) copolymer has a good thermostability and mold ability so that it can be processed into a strong string, or into a transparent, flexible film (Y. Doi, S. Kitamura, H. Abe, Macromolecules 28, 4822–4823, 1995).

*Pseudomonas* sp. strain 61-3 (JCM 10015) is known to contain polyester polymerases including PhaC1 (Japanese Laid Open Publication No. 10-276781, J. Bacteriol., 180, 6459–6467, 1998) and PhaC2 (J. Bacteriol., 180, 6459–46467, 1998), which can use various 3HA units whose carbon number ranges from 4 to 12 as substrates. However, copolymer polyester produced by *Pseudomonas* sp. strain 61-3 is not a preferable plastic material because it becomes amorphous due to its low 3HB composition.

DESCRIPTION OF THE INVENTION

An object of the present invention is to provide a transformant that is obtained by transforming a host, whose polyhydroxybutanoic acid polymerase gene is disrupted, with a recombinant vector containing a polyester polymerase gene, a β-ketothiolase gene, and a NADPH-acetoacetyl CoA reductase gene, and a method of producing a copolymer polyester with a high composition of 3HB using the transformant.

As a result of thorough studies on the above problems, the present inventors have completed the invention by finding that transformants obtained by transforming *Pseudomonas* sp. strain 61-3, whose polyhydroxybutanoic acid polymerase gene is disrupted, with a recombinant vector containing a polyester polymerase 1 gene derived from *Pseudomonas* sp. strain 61-3 (phaC1 gene), a β-ketothiolase gene (phbA gene) derived from *Ralstonia eutropha*, and a NADPH-acetoacetyl CoA reductase gene (phbB gene) derived from *Ralstonia eutropha*, produce a P(3HB-co-3HA) having molar composition of 3HB ranges from 80 to 95% and having 3HA units with a carbon number of 4 to 12.

In other words, the present invention provides a transformant that is obtained by transforming a host, whose polyhydroxybutanoic acid polymerase gene is disrupted, with a recombinant vector containing a polyester polymerase gene, β-ketothiolase gene, and NADPH-acetoacetyl CoA reductase gene.

The present invention provides a transformant wherein the polyester polymerase gene comprises a DNA encoding the following protein (a) or (b):
  (a) a protein having an amino acid sequence represented by SEQ ID NO: 2 or 4, or
  (b) a protein having an amino acid sequence including deletion, substitution, or addition of one or more amino acids relative to the amino acid sequence represented by SEQ ID NO: 2 or 4, and having polyester polymerase activity.

Further, the present invention provides a transformant wherein the polyester polymerase gene comprises the following DNA (a) or (b):
  (a) a DNA containing a nucleotide sequence represented by SEQ ID NO: 1 or 3, or
  (b) a DNA hybridizing to a DNA containing a nucleotide sequence of SEQ ID NO: 1 or 3 under stringent conditions, and encoding a protein with polyester polymerase activity.

Further, the present invention provides a transformant wherein the β-ketothiolase gene comprises a DNA encoding the following protein (a) or (b):
(a) a protein having an amino acid sequence represented by SEQ ID NO: 6, or
(b) a protein having an amino acid sequence including deletion, substitution, or addition of one or more amino acids relative to the amino acid sequence represented by SEQ ID NO:6, and having β-ketothiolase gene activity.

Further, the present invention provides a transformant wherein the β-ketothiolase gene comprises the following DNA (a) or (b):
(a) a DNA having an nucleotide sequence represented by SEQ ID NO: 5, or
(b) a DNA hybridizing to a DNA containing a nucleotide sequence of SEQ ID NO: 5 under stringent conditions and encoding a protein with β-ketothiolase activity.

Further, the present invention provides a transformant wherein the NADPH-acetoacetyl CoA reductase gene comprises a DNA encoding the following protein (a) or (b):
(a) a protein having an amino acid sequence represented by SEQ ID NO:8, or
(b) a protein having an amino acid sequence including deletion, substitution or addition of one or more amino acids relative to the amino acid sequence represented by SEQ ID NO: 8, and having NADPH-acetoacetyl CoA reductase activity.

Furthermore the present invention provides a transformant wherein the NADPH-acetoacetyl CoA reductase gene comprises the following DNA (a) or (b):
(a) a DNA having a nucleotide sequence represented by SEQ ID NO: 7, or
(b) a DNA hybridizing to a DNA containing a nucleotide sequence of SEQ ID NO: 7 under stringent conditions, and encoding a protein with NADPH-acetoacetyl CoA reductase activity.

Furthermore, the present invention provides a transformant which is a bacterium belonging to the genus Pseudomonas or Ralstonia. An example of the bacterium belonging to the genus Pseudomonas is the genus Pseudomonas sp. strain 61-3.

The present invention also provides a method of producing copolymer polyester which comprises the steps of culturing a transformant, and collecting polyester (for example, a polyester comprising 3-hydroxyalkanoic acid units with a carbon number of 4 to 12) from the culture product. An example of the polyester produced herein comprises 3-hydroxyalkanoic acid units with a carbon number of 4 to 12 wherein molar composition of 3-hydroxybutanoic acid is 80 to 95% molar fraction.

Detailed description of this invention will now be given as follows.

1. A Host for Transformation

Hosts that can be used for transformation are not specifically limited so far as they can express each gene contained in a recombinant vector. Examples of the host include bacteria belonging to the genus Pseudomonas, such as Pseudomonas putida, Pseudomonas sp. strain 61-3, those belonging to the genus Ralstonia, such as Ralstonia eutropha, those belonging to the genus Bacillus, such as Bacillus subtilis, those belonging to the genus Escherichia, such as Escherichia coli, yeast belonging to the genus Saccharomyces, such as Saccharomyces cerevisiae, yeast belonging to the genus Candida, such as Candida maltosa, and animal cells, such as COS cells and CHO cells.

In particular, a cell whose certain naturally occuring polyester polymerase gene is disrupted can be used to allow the host cell to produce a polyester having a desired composition. FIG. 1 shows the synthetic pathway of polyhydroxybutanoic acid (P(3HB)), and of a copolymer (P(3HB-co-3HA)) of 3-hydroxybutanoic acid and 3-hydroxyalkanoic acid.

The Pseudomonas sp. strain 61-3, whose polyhydroxybutanoic acid polymerase gene is disrupted, can be constructed by deleting the terminus of a polyhydroxybutanoic acid polymerase gene to cause mutation in the gene, and introducing the mutated gene into Pseudomonas sp. strain 61-3 to cause homologous recombination between the mutated polyhydroxybutanoic acid polymerase gene and a polyhydroxybutanoic acid polymerase gene on a chromosome. Whether the polyhydroxybutanoic acid polymerase gene is disrupted or not can be confirmed by Southern hybridization using a part of the gene as a probe. That is, it can be confirmed by examining if a band of hybridization shifts to an expected position relative to a band of a wild type.

2. Recombinant Vector

Recombinant vectors of this invention can be obtained by ligating (inserting) a polyester polymerase gene, β-ketothiolase gene, and NADPH-acetoacetyl CoA reductase gene into an appropriate expression vector.

Examples of the polyester polymerase gene include a phaC1 gene or a phaC2 gene derived from Pseudomonas sp. strain 61-3. A nucleotide sequence of the phaC1 gene is shown in SEQ ID NO: 1, and an amino acid sequence of the polyester polymerase encoded by the phaC1 gene is shown in SEQ ID NO: 2. Mutations including deletion, substitution, and addition of one or more amino acids may occur in the amino acid sequence so far as proteins having these amino acid sequences have polyester polymerase activity. For example, one, preferably 2 to 5, more preferably 5 to 10 amino acids may be deleted from the amino acid sequence represented by SEQ ID NO: 2 or 4; or one, preferably 2 to 5, more preferably 5 to 10 amino acids may be added to the amino acid sequence represented by 2 or 4; or one, preferably 2 to 5, more preferably 5 to 10 amino acids may be substituted in the amino acid sequence represented by SEQ ID NO: 2 or 4. Alternatively, a DNA which can hybridize to a DNA having a nucleotide sequence represented by SEQ ID NO: 1 or 3 under stringent conditions can also be used in this invention so far as the DNA encodes a protein having polyester polymerase activity. The stringent conditions include a temperature of 60 to 68° C., preferably 55 to 68° C., and a sodium concentration of 250 to 350 mM, preferably 300 to 400 mM.

An example of a β-ketothiolase gene is a phbA gene derived from Ralstonia eutropha. A nucleotide sequence of the phbA gene is shown in SEQ ID NO:5, and an amino acid sequence of the β-ketothiolase encoded by the phbA gene is shown in SEQ ID NO:6. So far as proteins having these amino acid sequences possess β-ketothiolase activity, mutations including deletion, substitution, and addition of one or more amino acids may occur in these amino acid sequences. For example, one, preferably 2 to 5, more preferably 5 to 10 amino acids may be deleted from the amino acid sequence represented by SEQ ID NO: 6; or one, preferably 2 to 5, more preferably 5 to 10 amino acids may be added to the amino acid sequence represented by SEQ ED NO: 6; or one, preferably 2 to 5, more preferably 5 to 10 amino acids may be substituted in the amino acid sequence represented by SEQ ID NO: 6. Alternatively, a DNA which can hybridize to a DNA having a nucleotide sequence represented by SEQ ID NO: 5 under stringent conditions can also be used in this invention so far as the DNA encodes a protein having β-ketothioesterase activity. The stringent conditions include a temperature of 60 to 68° C., preferably 55 to 68° C., and sodium concentration of 250 to 350 mM, preferably 300 to 400 mM.

An example of a NADPH-acetoacetyl CoA reductase gene is a phbB gene derived from Ralstonia eutropha. A nucleotide sequence of the phbB gene is shown in SEQ ID NO:7, and an amino acid sequence of the NADPH-acetoacetyl CoA reductase encoded by the phbB gene is shown in SEQ ID NO: 8. So far as proteins having these amino acid sequences possess NADPH-acetoacetyl CoA reductase activity, mutations including deletion, substitution, and addition of one or more amino acids may occur in these amino acid sequences. For example, one, preferably 2 to 5, more preferably 5 to 10 amino acids may be deleted from the amino acid sequence represented by SEQ ID NO: 8; or one, preferably 2 to 5, more preferably 5 to 10 amino acids may be added to the amino acid sequence represented by SEQ ID NO: 8; or one, preferably 2 to 5, more preferably 5 to 10 amino acids may be substituted in the amino acid sequence represented by SEQ ID NO: 8. Alternatively, a DNA which can hybridize to a DNA having a nucleotide sequence represented by SEQ ID NO: 7 under stringent conditions can also be used in this invention so far as the DNA encodes a protein having NADPH-acetoacetyl CoA reductase activity. The stringent conditions include a temperature of 60 to 68° C., preferably 55 to 68° C., and sodium concentration of 250 to 350 nM, preferably 300 to 400 mM.

Vectors used herein to insert each gene as described above are not specifically limited so far as they can autonomously replicate in hosts. Examples of the vector include plasmid DNA and phage DNA. When Escherichia coli is used as a host cell, examples of vectors include plasmid DNAs, such as pBR322, pUC18, and pBluescript II, phage DNAs, such as EMBL3, M13, and λgt11. When yeast is used as a host cell, examples of vectors include YEp13 and YCp50; when an animal cell is used as a host cell, examples of vectors include pcDNAI, and pcDNAI/Amp (Invitrogen). In addition, when bacteria belonging to the genus Ralstonia and those belonging g to the genus Pseudomonas are used as host cells, examples of vectors include pLA2917 (ATCC37355) having RK2 replication origin, and pJRD215 (ATCC 37533) having RSF1010 replication origin. These replication origins are replicated and retained in a broad range of hosts.

A gene can be inserted into a vector by integrating a DNA fragment with the above gene into a vector DNA fragment digested with a restriction enzyme. At this time, the above gene must be inserted into a vector so that the gene function is exhibited. Particularly, gene expression requires insertion of a gene downstream of a promoter. Any promoter can be used so far as it can express in a host. When Escherichia coli is used as a host cell, examples of promoters include tip promoter, lac promoter, PL promoter, PR promoter, and T7 promoter; when yeast is used as a host cell, examples of promoters include gall promoter and gal 10 promoter.

When bacteria belonging to the genus Pseudomonas are used as host cells, a promoter region of upstream of a phaC1$_{Ps}$ gene or a phbCAB$_{Re}$ gene may be used as a promoter. A nucleotide sequence of upstream of the phaC1$_{Ps}$ gene is as shown in SEQ ID NO: 9, and that of upstream of the phbCAB$_{Re}$ operon is as shown in SEQ ID NO: 10.

If necessary, a terminator, enhancer, splicing signal, polyA additional signal, selection marker, and ribosome binding sequence (SD) and the like may be integrated into the vector of this invention. Examples of the selection marker include ampicillin-, tetracycline-, neomycin-, kanamycin, and chroramphenicol-resistant genes. Particularly when bacteria belonging to the genus Pseudomonas are used as host cells, a terminator region of downstream of a phbCAB$_{Re}$ operon may be used as a terminator. A nucleotide sequence downstream of the phbCAB$_{Re}$ operon is as shown in SEQ ID NO: 11.

3. Preparation of Transformants

The transformant of this invention can be obtained by introducing a recombinant vector obtained in 2 above into a host cell of 1 above. Examples of a method of introducing a recombinant DNA into a bacterium include a method using calcium ions (Current Protocols in Molecular Biology, vol. 1, p.1.8.1, 1994) or electroporation (Current Protocols in Molecular Biology, vol. 1, p.1.8.4, 1994). A plasmid can be introduced into a bacterium belonging to the genus Pseudomonas by the conjugation transfer method (Friedrich et al.:J. Bacteriol. 147: 198–205, 1981).

Examples of a method of introducing a recombinant DNA into yeast include electroporation (Methods. Enzymol., 194: 182–187, 1990), the spheroplast method (Proc. Natl. Acad. Sci., USA, 84:1929–1933 (1978)), the lithium acetate method (J. Bacteriol., 153:163–168, 1983). Examples of a method of introducing a recombinant DNA into an animal cell include electroporation and the calcium phosphate method.

The transformant (strain) Pseudomonas sp. BB49 obtained by transforming Pseudomonas sp. strain 61-3, whose polyhydroxybutanoic acid polymerase gene is disrupted, with a plasmid pJBB49-phb, and the transformant Pseudomonas sp. KSc46 obtained by transforming with a plasmid pJKSc46-pha, and the transformant Pseudomonas sp. KSc54 obtained by transforming with a plasmid pJKSc54-phb were deposited with National Institute of Bioscience and Human-Technology, National Institute of Advanced Industrial Science and Technology (1-1-3, Higashi 1-chome, Tsukuba-shi, Ibaraki-ken, Japan) on Aug. 5, 1999. The accession numbers received were FERM BP-7263, FERM BP-7264 and FERM BP-7265, respectively.

4. Production of Polyester

Polyester is produced by culturing the transformants of this invention in media, allowing them to synthesize and accumulate copolymer polyester in the culture cells or culture products, and collecting the polyester from the culture cells or culture products. The transformants of this invention are cultured in media by standard methods employed for culturing hosts.

Examples of culture media for culturing transformants obtained using bacteria belonging to the genus Ralstonia or the genus Pseudomonas as host cells include media containing carbon sources assimilable by microorganisms, and containing a limited amount of any one of nitrogen sources, inorganic salts, or other organic nutrient sources. For example, a medium used herein contains nitrogen sources limited to 0.01% to 0.1%. Culture is performed at 25 to 37° C. aerobically for 2 to 7 days to allow the cells to accumulate polyester within the cells, followed by collection of the polyester.

Examples of carbon sources include carbohydrates such as glucose, fructose, sucrose, and maltose. Oil and fat-related substances with a carbon number of 4 or more than 4 may be used as carbon sources. Examples of such carbon sources include natural oil, such as corn oil, soy oil, safflower oil, sunflower oil, olive oil, palm oil, colza oil, fish oil, whale oil, pig oil, or cattle oil; fatty acids, such as butanoic acid, pentanoic acid, hexanoic acid, octanoic acid, decanoic acid, lauric acid, oleic acid, palmitin acid, linoleic acid, linolic acid or myristic acid, or esters of these fatty acids; octanol, lauryl alcohol, oleyl alcohol, or palmityl alcohol, or esters of these alcohols.

Examples of nitrogen sources include ammonia, ammonium salts such as ammonium chloride, ammonium sulfate, and ammonium phosphate in addition to in peptone, meat extract, yeast extract, corn steep liquor. Examples of inorganic substances include potassium phosphate, potassium secondary phosphate, magnesium phosphate, magnesium sulfate, sodium chloride.

Normally, shake-culture is performed under aerobic conditions at 25 to 37° C. for 24 hours or more following induction of expression. Antibiotics including kanamycin, ampicillin, and tetracycline may be added to media while culturing.

When a transformant (microorganisms) transformed by an expression vector containing an inducible promoter is cultured, an inducer may be added to the medium. For example, isopropyl- β-D-thiogalactoside (IPTG), indoleacrylic acid (IAA) and the like may be added to the media.

Examples of media for culturing transformants obtained using animal cells as host cells include RPMI-1640 media, DMEM media, or those supplemented with fetal calf serum. Culturing is usually performed in the presence of 5% $CO_2$ at 30 to 37° C. for 14 to 28 days. Antibiotics including kanamycin and penicillin may be added to the media.

Polyester of this invention can be purified as follows. Transformants are collected by centrifugation from culture solution, washed with distilled water, and then dried. Next, the dried transformants are suspended in chloroform and heated to extract polyester. Residue is removed by filtration. Then methanol is added to the chloroform solution to precipitate polyester. Following removal of supernatant by filtration and centrifugation, the product is dried to obtain purified polyester. The resulting polyester can be used as materials for biodegradable strings, films, and various containers. Whether the resulting polyester is of interest or not is confirmed by standard techniques including gas chromatography and nuclear magnetic resonance methods.

EXAMPLES

Figure 1:
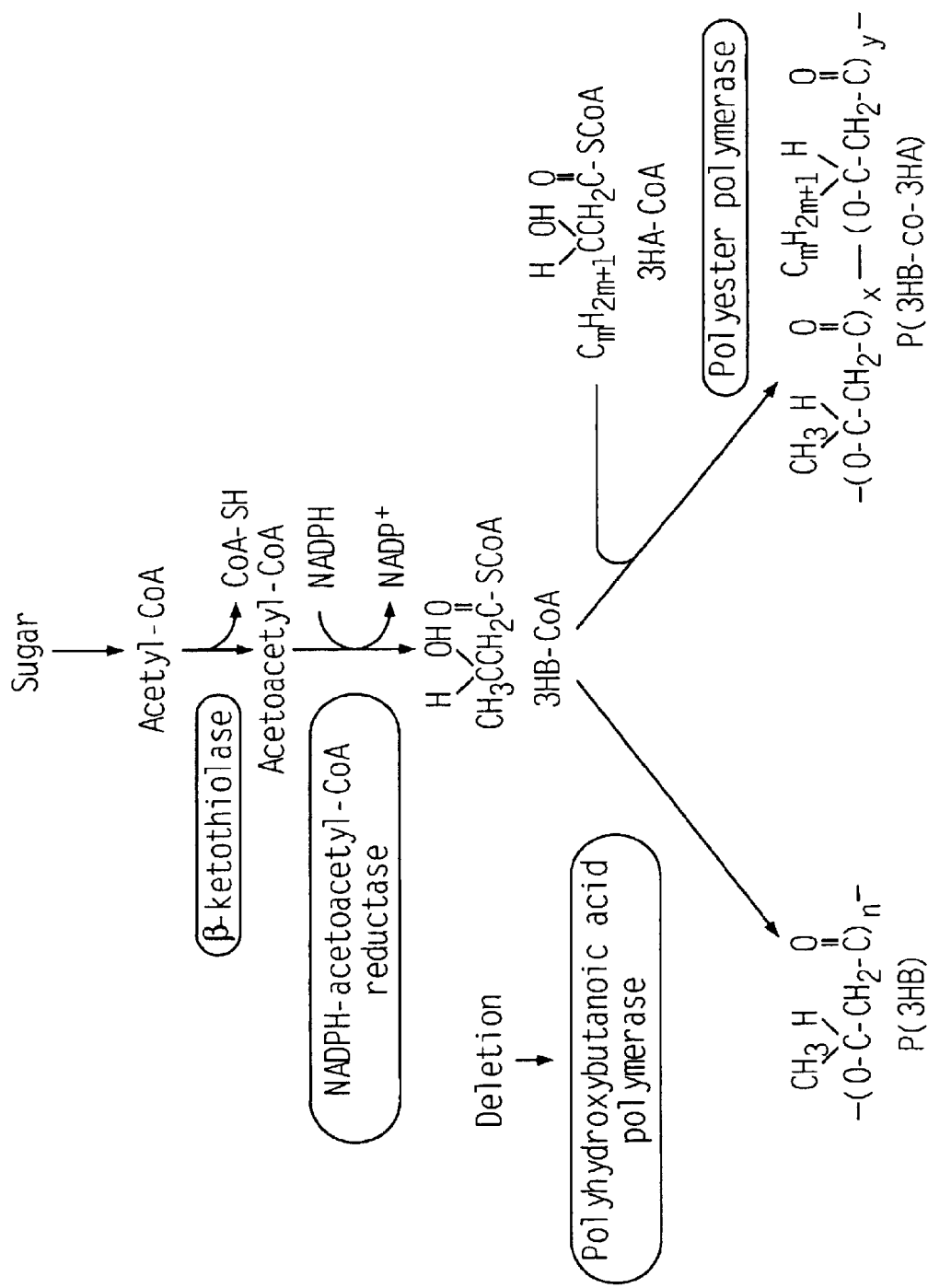
FIG. 1 shows a synthetic pathway of polyester.
Figure 2A:
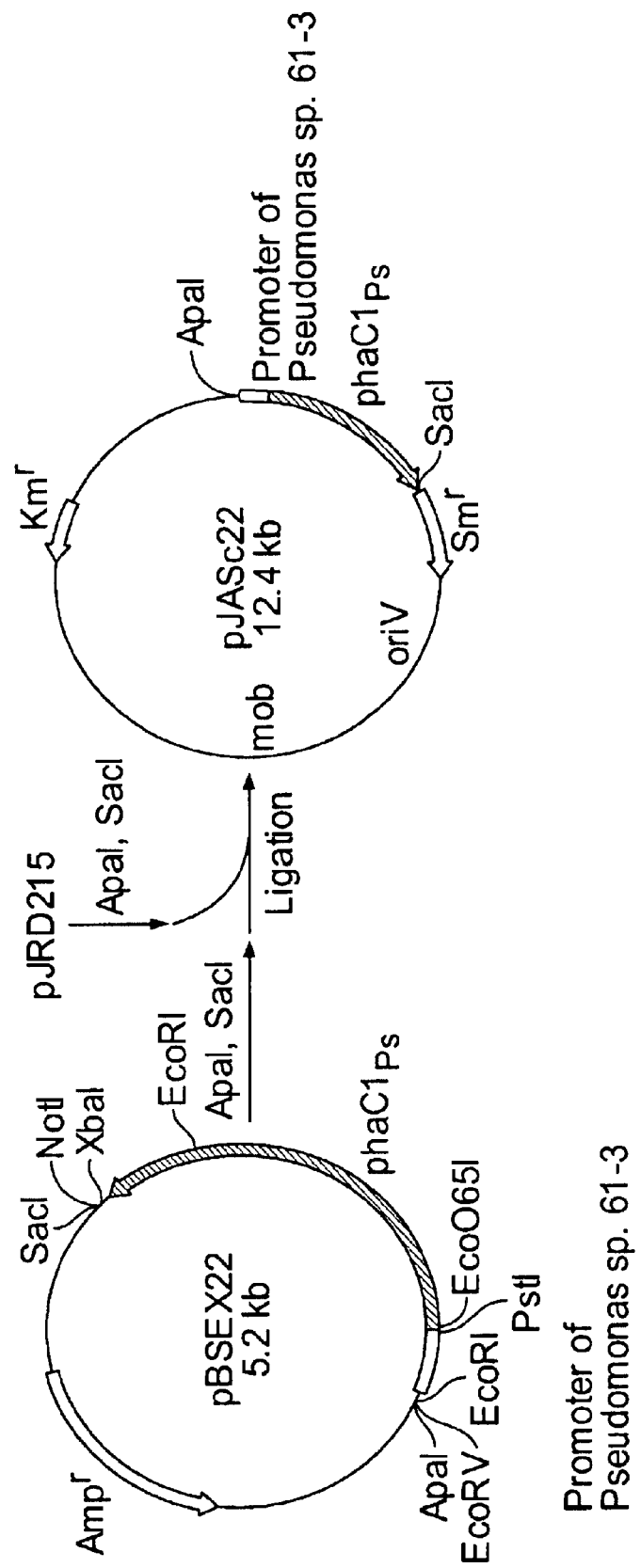
FIGS. 2A–2F show steps to construct a recombinant vector.
Figure 2B:
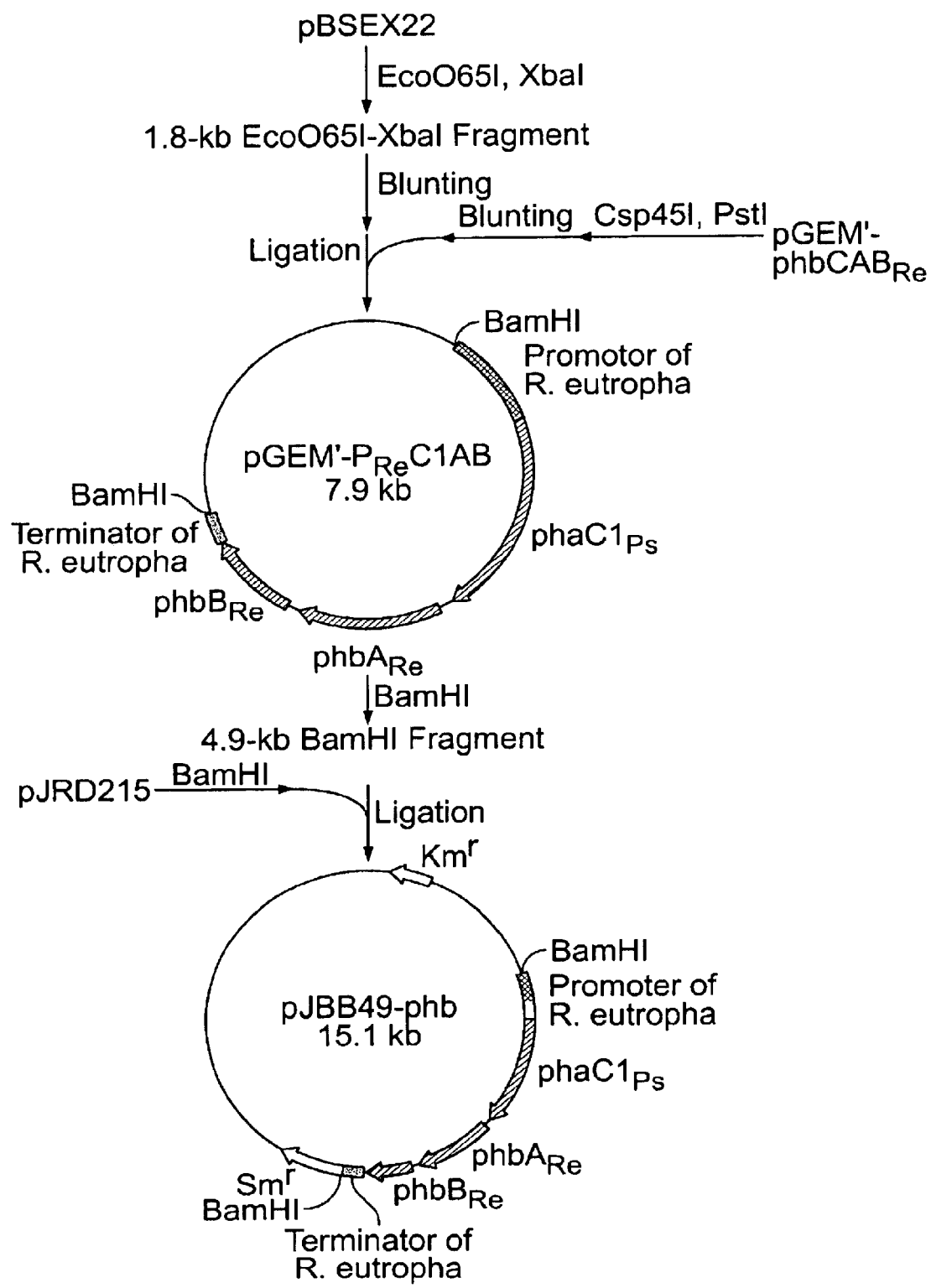
Figure 2C:
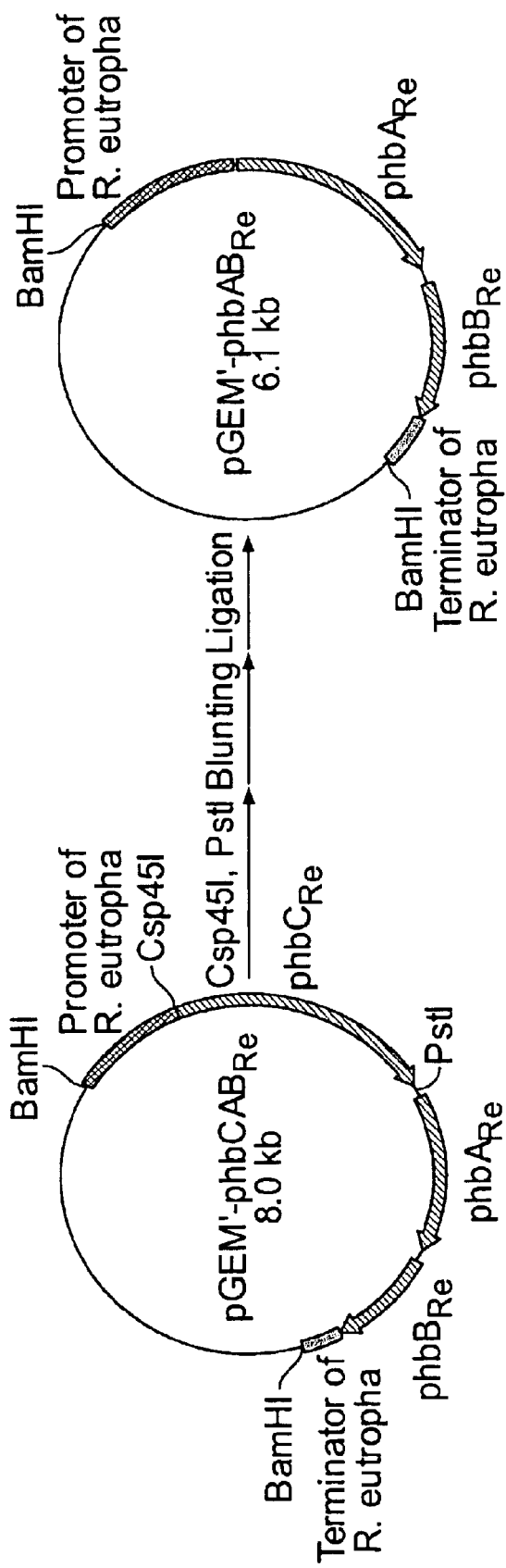
Figure 2D:
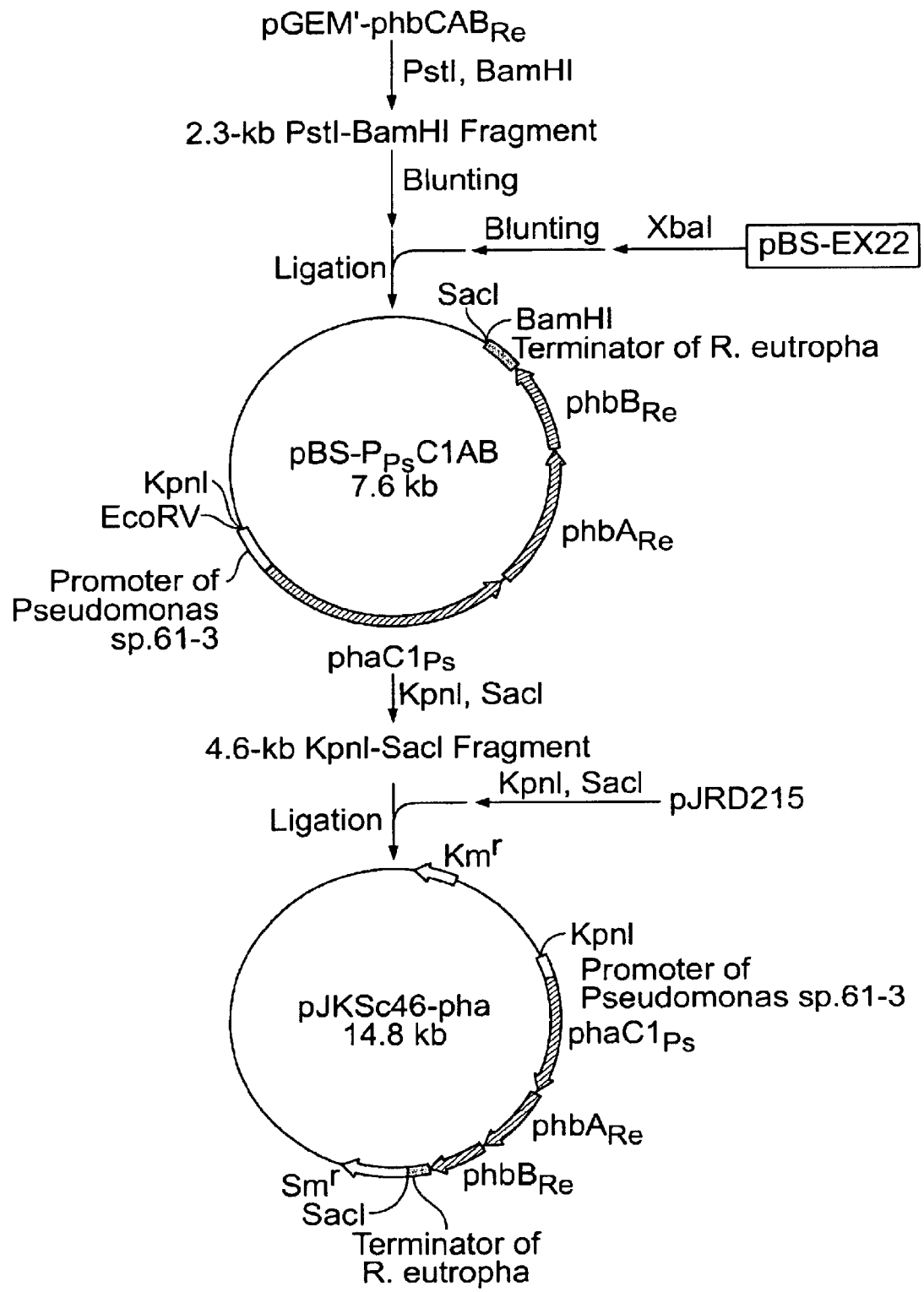
Figure 2E:
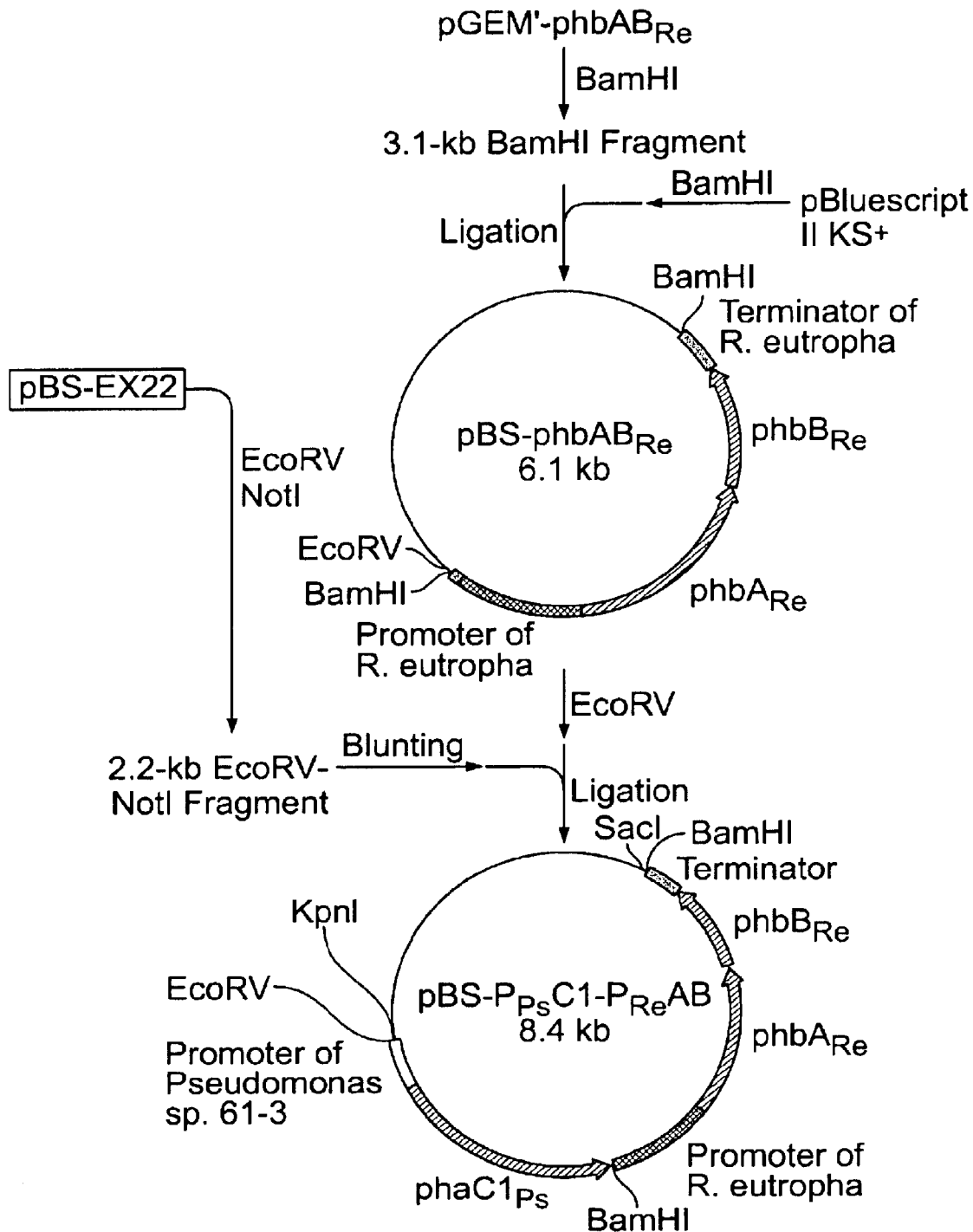
Figure 2F:
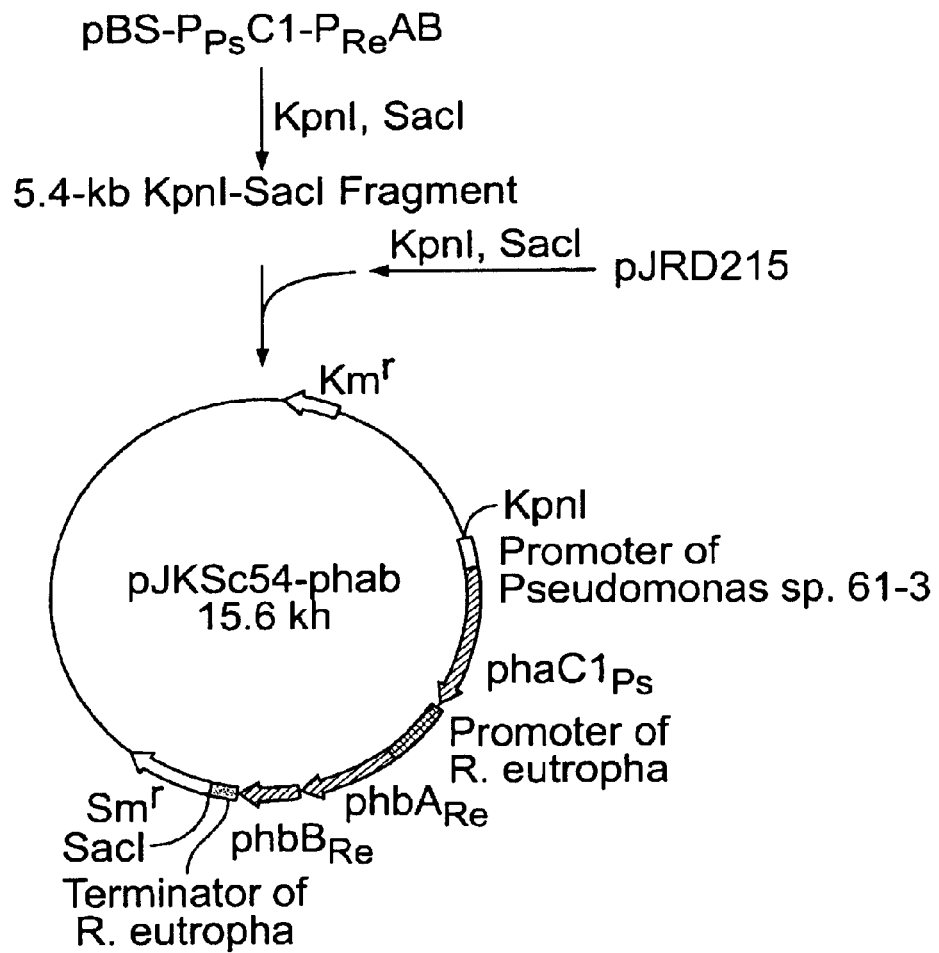

A detailed description of the present invention will be given as follows. However, the technical scope of the present invention is not limited by the examples.

Example 1

Establishment of a Polyhydroxybutanoic Acid Polymerase Gene-disruptant of *Pseudomonas* sp. Strain 61-3

*Pseudomonas* sp. strain 61-3 (JCM 10015) contains polyhydroxybutanoic acid polymerase (PhbC) in addition to polyhydroxyalkanoic acid polymerase (PhaC1 and PhaC2) that can use a broad range of substrates with a carbon number of 4 to 12. Therefore, this strain 61-3 synthesizes a blend of polyester (P(3HB)) having a sole unit of 3-hydroxybutanoic acid and copolymer polyester (P(3HB-co-3HA)) containing 3HA units with a carbon number of 4 to 12. A 3HB unit is often favored in comparison to PhaC1 or PhaC2 as a substrate by PhbC, which has a high affinity with the 3HB unit, so that copolymer polyester with a high 3HB molar composition is not synthesized. Accordingly, a polyhydroxybutanoic acid polymerase gene-disruptant of *Pseudomonas* sp. strain 61-3 was established.

First, the 5' terminal region of 342 bp and the 3' terminal region of 418 bp were deleted from a gene phbC$_{Ps}$ gene) encoding polyhydroxybutanoic acid polymerase of *Pseudomonas* sp. strain 61-3, thereby preparing a deleted polyhydroxybutanoic acid polymerase gene fragment (EcoRI-PstI fragment) of 941 bp. Next, the resulting EcoRI-PstI fragment was ligated to EcoRI and PstI sites of pBR322, thereby constructing a plasmid pBREP9 (Tc$^r$) for disrupting polyhydroxybutanoic acid polymerase gene. The obtained plasmid pBREP9 (Tc$^r$) was introduced into *Pseudomonas* sp. strain 61-3 suspended in 8 mM HEPES buffer (pH 7.2) containing 272 mM sucrose by electroporation (conditions: 7.5 kV/cm, 800Ω, 25 μF). phbC$_{Ps}$ gene-disrupted strain (phbC::tet) was screened for strains capable of growing on LB media containing tetracyclin. Then chromosomal DNAs prepared from some of the screened strains and wild strains were digested with appropriate restriction enzymes. Following digestion, Southern hybridization with a part of phbC$_{Ps}$ gene as a probe was performed, thereby selecting and obtaining strains showing a band that had shifted to a position of an expected molecular weight.

Example 2

Construction of a Recombinant Vector

FIG. 2 shows steps to construct a recombinant vector. Cleavage and ligation of DNA fragments were performed according to standard techniques (Sambrook et al.: Molecular Cloning, A Laboratory Manual $2^{nd}$ ed., Cold Spring Harbor Laboratory Press, 1989). As shown in FIG. 2, pBSEX22 and pGEM'-phbCAB were used as start plasmids. Here, pBSEX22 was constructed by inserting a 2.2-kb EcoRI-XbaI region containing phaC1 gene of *Pseudomonas* sp. strain 61-3 into pBluescript II KS+. pGEM'-phbCAB was constructed by amplifying phbCAB gene of *Ralstonia eutropha* H16 (ATCC 17699) (J. Biol. Chem., 264, 15293–15297, 1989; J. Biol. Chem., 264, 15298–15303, 1989) by PCR and inserting the resulting PCR fragment into a pGEM-T (Promega) vector having disrupted NdeI and PstI sites.

Figure 3:
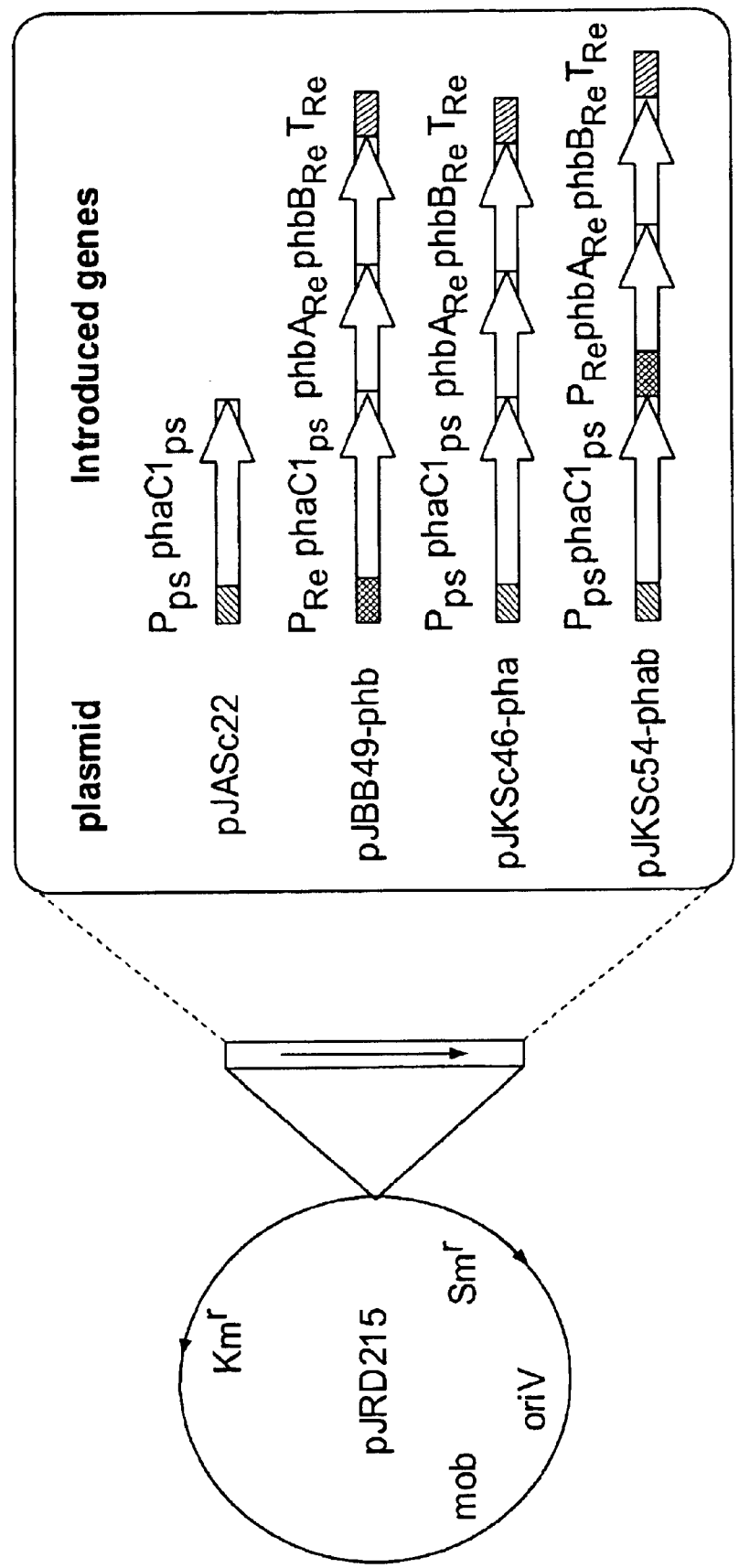
FIG. 3 shows a structure of the recombinant vector used for transformation of *Pseudomonas* sp. strain 61-3 (phbC::tet).

At the final step of the construction of a recombinant vector, the DNA fragment encoding a gene of interest was inserted and ligated into a plasmid pJRD215 (ATCC37533) capable of replicating within *Pseudomonas* sp. strain 61-3. In other words, a plasmid pJASc22 was constructed by cutting out a ApaI-SacI fragment which contains polyester polymerase 1 gene (phaC1$_{Ps}$ gene) derived from *Pseudomonas* sp. strain 61-3 and a promoter (P$_{Ps}$ promoter) of this gene from pBSEX22, and by inserting and ligating the fragment into ApaI and SacI sites of pJRD215. Further, a plasmid pJBB49-phb was constructed by inserting and ligating BamHI-BamHI fragment which contains phbCAB$_{Re}$ operon promoter (P$_{Re}$ promoter) derived from *Ralstonia eutropha*, phaC1$_{Ps}$ gene, β-ketothiolase gene (phbA$_{Re}$ gene) derived from *Ralstonia eutropha*, NADPH-acetoacetyl CoA reductase gene (phbB$_{Re}$ gene) derived from *Ralstonia eutropha*, and phbCAB$_{Re}$ operon terminator (T$_{Re}$ terminator) derived from *Ralstonia eutropha* into a BamHI site of pJRD215. Furthermore, a plasmid pJKSc46-pha was constructed by inserting and ligating KpnI-SacI fragment, which contains $P_{Ps}$ promoter, phaC1$_{Ps}$ gene, phbA$_{Re}$ gene, phbB$_{Re}$ gene and T$_{Re}$ terminator into KpnI and SacI sites of pJRD215. Moreover, a plasmid pJKSc54-phab was constructed by inserting and ligating KpnI-SacI fragment, which contains $P_{Ps}$ promoter, phaC1$_{Ps}$ gene, $P_{Re}$ promoter, phbA$_{Re}$ gene, phbB$_{Re}$ gene and T$_{Re}$ terminator, into KpnI and SacI sites of pJRD215. Structures of the four types of plasmids obtained are shown in FIG. 3.

Example 3

Construction of a *Pseudomonas* sp. Strain 61-3 (phbC::tet) Transformant

A transformant was constructed by introducing the plasmid obtained in Example 2 into the phbC$_{Ps}$ gene-disruptant phbC::tet) of *Pseudomonas* sp. strain 61-3 obtained in Example 1 by the conjugation transfer method. That is, four types of plasmids pJASc22, pJBB49-phb, pJKSc46-pha, and pJKSc54-phab were separately transformed into *E.coli* strain S 17-1 by the calcium chloride method. Next, the obtained transformants and *Pseudomonas* sp. strain 61-3 (phbC::tet) were separately cultured overnight in 1.5 ml of LB medium at 37° C. and 28° C., respectively. Subsequently, 0.1 ml of the culture product of *E.coli* and 0.1 ml of that of *Pseudomonas* sp. strain 61-3(phbC::tet) were mixed and cultured for 4 hours at 28° C. After culturing, the mixture was plated over MS agar media (0.9% sodium diphosphate, 0.15% monopotassium phosphate, 0.05% ammonium chloride, 2% glucose, 0.1% (v/v) Trace element solution (COCl$_2$.6H$_2$O 0.218 g, FeCl$_3$ 9.7 g, CaCl$_2$ 7.8 g, NiCl$_3$.6H$_2$O 0.118 g, CrCl$_3$.6H$_2$O 0.105 g, and CuSO$_4$.5H$_2$O 0.156 g dissolved in 1 liter of 0.1N hydrochloric acid), 1.5% agar, 50mg/l kanamycin, 12.5 g/l tetracyclin) and cultured for 2 to 5 days at 28° C.

Transformants were obtained by isolating colonies that had grown on the MS agar medium. Four types of transformants having pJASc22, pJBB49-phb, pJKSc46-pha, and pJKSc54-phab were designated as *Pseudomonas* sp. strain ASc22, BB49, KSc46, and Ksc54, respectively.

Example 4

Polyester Synthesis by *Pseudomonas* sp. Strain 61-3 (phbC::tet) Transformants

Polyester was produced by transformants obtained in Example 3. First, each strain of *Pseudomonas* sp. 61-3 (phbC::tet), ASc22, BB49, KSc46, and KSc54 was inoculated in 100 ml of MS medium containing 2% glucose, and then cultured in Sakaguchi flasks (shaking flasks) for 48 hours at 28° C. Cells were collected by centrifugation, washed with distilled water, and freeze-dried. The dried cells were measured for weight, polyester content, and polyester composition.

That is, 2 ml of a mixture of sulfuric acid—methanol (15:85) and 2 ml of chloroform were added to 10 to 30 mg of the dried cells, then the containers were tightly stoppered. Then, methyl ester was obtained by decomposing intracellular polyester by heating for 140 minutes at 100° C. Then 1 mil of distilled water was added to the methyl ester, followed by vigorous stirring. Next the mixture was allowed to stand to separate into two layers. The organic layer of the lower layer was taken out and the composition was analyzed by capillary gas chromatography. A gas chromatograph used herein was GC-17A (manufactured by SHIMADZU CORPORATION) and capillary column was NEUTRA BOND-1 (manufactured by GL Science, column length 25 m, column internal diameter 0.25 mm, liquid film thickness 0.4 μm). Temperature was raised at a rate of 8° C./min from the initial temperature of 100° C. Table 1 shows the results.

TABLE 1

Copolymer polyester production by *Pseudomonas* sp. strain 61-3 (phbC::tet)

| Strain | Dry cell weight (g/l) | Polyester content (wt %) | Polyester composition (mol %) | | | | | |
|---|---|---|---|---|---|---|---|---|
| | | | 3HB (C$_4$) | 3HHx (C$_6$) | 3HO (C$_8$) | 3HD (C$_{10}$) | 3HDD (C$_{12}$) | 3H5DD (C$_{12}$) |
| phbC::tet | 0.7 | 4 | 36 | 0 | 6 | 23 | 20 | 15 |
| Asc22 | 0.7 | 6 | 64 | 0 | 2 | 15 | 11 | 8 |
| BB49 | 1.7 | 38 | 92 | 0 | 1 | 4 | 2 | 1 |
| Ksc46 | 2.6 | 37 | 81 | 0 | 1 | 9 | 5 | 4 |
| Ksc54 | 2.5 | 45 | 92 | 0 | 1 | 3 | 3 | 1 |

Note) 3HB: 3-hydroxybutanoic acid; 3HHx: 3-hydroxyhexanoic acid; 3HO: 3-hydroxyoctanoic acid, 3HD: 3-hydroxydecanoic acid; 3HDD: 3-hydroxydodecanoic acid, 3H5DD: 3-hydroxy-cis-5-dodecanoic acid As clearly shown in Table 1, each type of recombinant cell achieved relatively efficient accumulation of 5 to 50 wt % polyester using 2 % glucose as a carbon source. *Pseudomonas* sp. strain 61-3 (phbC::tet) produced copolymer polyester P(3HB-co-3HA) having a 3HB molar composition of 36 mol %, while the strain ASc22 with the introduced phaC1 gene produced polyester having a 3HB molar composition of approximately 64 mol %, slightly higher than that of the former polyester. On the other hand, the strains BB49, KSc46, and KSc54, into which phbA and phbB genes derived from *Ralstonia eutropha* had been introduced, produced polyester having as high as 81 to 92 mol % of a 3HB molar composition. Moreover, these strains accumulated polyester in the cells at a high intracellular accumulation ratio of 37 to 45 wt %. Unlike P(3HB), copolymer polyester P(3HB-co-3HA) with a high 3HB molar composition has better flexibility and good impact resistance. Therefore, it is concluded that more practical biodegradable plastic can be produced at higher efficiency by using the above described strains.

Example 5

Mechanical Strength of Copolymer Polyester

Figure 4:
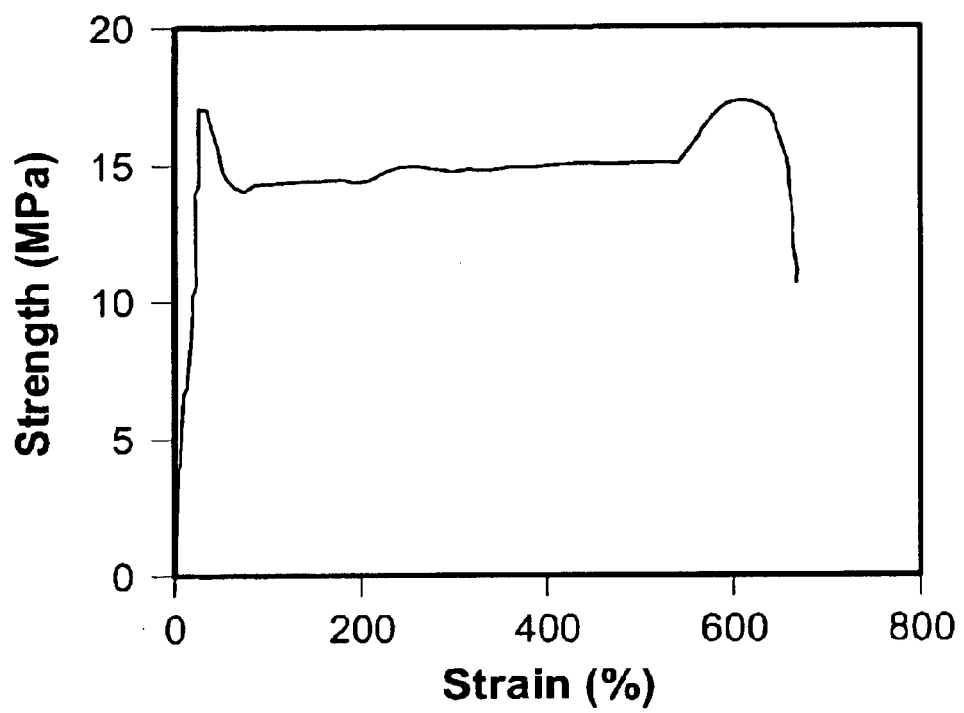
FIG. 4 shows the results of tensile test on copolymer polyester film obtained by this invention.

Mechanical strength of the copolymer polyester with a high 3HB molar composition obtained in this invention was examined. First, a film with a thickness of approximately 150 μm was prepared using copolymer polyester P(3HBco-3HA) consisting of 94 mol % 3-hydroxybutanoic acid (carbon number: 4) and 6 mol% 3-hydroxyalkanoic acid (carbon number: 6 to 12). Then a tensile test was performed on the film at a tensile strength of 100 mm/min and at room temperature according to the method of Doi, Y. et al. (Macromolecules 28: 4822, 1995). FIG. 4 shows the result. Tensile strength, Young's modulus, and elongation to break calculated based on a curve as shown in FIG. 4 were 17 MPa, 0.22Gpa, and 680%, respectively. These values are equivalent to those of low density polyethylene, which is made from general petroleum (film grade; 10 MPa, 0.17 GPa, and 620%). In addition, known biodegradable copolymer polyesters P(3HB-co-10% 4HB) (Saito, Y. et al. : Int. J. Biol. Macromol., 16: 99, 1994) and P(3HB-co-10% 3HHx) (Doi, Y et al. : Macromolecules 28: 4822, 1995) have a tensile strength of 24 MPa and 21 MPa, and fracture elongation percentage of 242% and 400%, respectively.

Thus, the biodegradable copolymer polyester obtained in this invention is confirmed to have flexibility superior to known biodegradable polyesters.

As described above, biodegradable plastic with mechanical strength equivalent to that of petroleum plastic, and high flexibility that known types of degradable plastic lack was able to be produced according to the present invention.

Industrial Applicability

A method of this invention is to synthesize copolymer polyester P(3HB-co-3HA) comprising 3-hydroxyalkanoic acid units with a carbon number of 4 to 12 and having a high 3HB molar composition. Such a polyester is useful because it has good thermal stability and mold ability, and can be made into biodegradable plastic with impact resistance better than that of P(3HB).

What is claimed is:

1. A transformant comprising a host cell, wherein the polyhydroxybutanoic acid polymerase gene in the host cell is disrupted with a recombinant vector containing a polyester polymerase gene, a β-ketothiolase gene, and a NADPH-acetoacetyl CoA reductase gene, wherein the polyester polymerase gene comprises a DNA encoding a protein selected from the group consisting of:

(a) a protein having an amino acid sequence represented by SEQ ID NO:2 or 4, and (b) a protein having an amino acid sequence including deletion, substitution, or addition of between 2 and 10 amino acids relative to the amino acid sequence represented by SEQ ID NO:2 or 4, and having polyester polymerase activity, wherein the β-ketothiolase gene comprises a DNA encoding a protein selected from the group consisting of:

(a) a protein having an amino acid sequence represented by SEQ ID NO:6, and (b) a protein having an amino acid sequence including deletion, substitution, or addition of between 2 and 10 amino acids relative to the amino acid sequence represented by SEQ ID NO:6, and having β-ketothiolase activity, and wherein the NADPH-acetoacetyl CoA reductase gene comprises a DNA encoding a protein selected from the group consisting of:

(a) a protein having an amino acid sequence represented by SEQ ID NO:8, and (b) a protein having an amino acid sequence including deletion, substitution, or addition of between 2 and 10 amino acids relative to the amino acid sequence represented by SEQ ID NO:8, and having NADPH-acetoacetyl CoA reductase activity.

2. The transformant of claim 1, wherein the polyester polymerase gene comprises a nucleotide sequence represented by SEQ ID NO: 1 or 3.

3. The transformant of claim 1, wherein the β-ketothiolase gene comprises a nucleotide sequence represented by SEQ ID NO:5.

4. The transformant of claim 1, wherein the NADPH-acetoacetyl CoA reductase gene comprises a nucleotide sequence represented by SEQ ID NO:7.

5. The transformant of claim 1 wherein the host cell is a bacterium belonging to the genus *Pseudomonas* or the genus *Ralstonia*.

6. The transformant of claim 5, wherein the bacterium belonging to the genus *Pseudomonas* is *Pseudomonas* sp. strain 61-3 (JCM10015).

7. A method of producing copolymer polyester comprising culturing the transformant of any one of claims 1, 2, 3, 4–6 and collecting polyester from the culture product.

8. The method of producing copolymer polyester of claim 7, wherein the polyester comprises 3-hydroxyalkanoic acid units with a carbon number of 4 to 12.

9. The method of producing copolymer polyester of claim 8, wherein the 3-hydroxyalkanoic acid units contain 3-hydroxyburanoic acid with 80 to 95% molar fraction.

* * * * *